(12) United States Patent
Zhong et al.

(10) Patent No.: US 12,665,582 B2
(45) Date of Patent: Jun. 23, 2026

(54) SYNERGISTIC PULSE GENERATION APPARATUS, DEVICE AND METHOD

(71) Applicant: HANGZHOU WKNIFE MEDICAL TECHNOLOGY CO., LTD, Hangzhou (CN)

(72) Inventors: Xinghua Zhong, Hangzhou (CN); Long Wang, Hangzhou (CN); Ke Yang, Hangzhou (CN)

(73) Assignee: Hangzhou Wknife Medical Technology Co., Ltd, Hangzhou (CN)

( * ) Notice: Subject to any disclaimer, the term of this patent is extended or adjusted under 35 U.S.C. 154(b) by 106 days.

(21) Appl. No.: 18/681,822

(22) PCT Filed: Aug. 11, 2022

(86) PCT No.: PCT/CN2022/111840
§ 371 (c)(1),
(2) Date: Feb. 6, 2024

(87) PCT Pub. No.: WO2023/016523
PCT Pub. Date: Feb. 16, 2023

(65) Prior Publication Data
US 2024/0339993 A1      Oct. 10, 2024

(30) Foreign Application Priority Data

Aug. 11, 2021    (CN) .......................... 202110921262.1
Aug. 11, 2021    (CN) .......................... 202110921264.0

(51) Int. Cl.
*H03K 3/53*        (2006.01)
*A61B 18/12*      (2006.01)
(Continued)

(52) U.S. Cl.
CPC ........... *H03K 3/53* (2013.01); *A61B 18/1206* (2013.01); *H03K 3/42* (2013.01); *A61B 2017/00176* (2013.01); *A61B 2018/00577* (2013.01)

(58) Field of Classification Search
CPC ........... H03K 3/53; H03K 3/57; H03K 3/017; H03K 3/42
See application file for complete search history.

(56) References Cited

U.S. PATENT DOCUMENTS 6,871,084 B1    3/2005  Kingsley et al.
7,301,250 B2   11/2007  Cassel
(Continued)

FOREIGN PATENT DOCUMENTS

CN          1183675  A        6/1998
CN      201903673  U    *    7/2011
(Continued)

OTHER PUBLICATIONS

Yu et al, "Electromagnetic Interference Resisting Operational Amplifier", 2014, IEEE, all pages (Year: 2014).*
(Continued)

*Primary Examiner* — Daniel C Puentes
(74) *Attorney, Agent, or Firm* — Ladas & Parry, LLP

(57)                ABSTRACT

Embodiments of the present application provide a cooperative pulse generation apparatus, device and generation method. The synergistic pulse generation apparatus comprises a drive circuit and a pulse generation circuit. The drive circuit receives a first control signal and a second control signal sent by a host computer, converts the first control signal into a first drive signal, and converts the second control signal into a second drive signal. The pulse generation circuit comprises a first power supply, a second power supply, a first pulse generation module, and a second pulse (Continued)

generation module. The first pulse generation module stores electric energy supplied by the first power supply and discharges the electricity under the control of the first drive signal to form a first pulse signal, and the second pulse generation module stores electric energy provided by the second power supply and discharges the electricity under the control of the second drive signal to form a second pulse signal. The present embodiment can selectively form a first pulse signal and/or a second pulse signal having different widths, thereby achieving the purpose of applying a composite pulse to a load.

17 Claims, 10 Drawing Sheets

(51) Int. Cl.
*H03K 3/42*        (2006.01)
*A61B 17/00*      (2006.01)
*A61B 18/00*      (2006.01)

(56)                    References Cited

U.S. PATENT DOCUMENTS

| | | | |
|---|---|---|---|
| 7,989,987 | B2 | 8/2011 | McDonald |
| 2006/0002050 | A1 | 1/2006 | Kichline, Jr. |
| 2012/0001498 | A1 | 1/2012 | Mayes |
| 2012/0224849 | A1 * | 9/2012 | Rylyakov ......... H04B 10/25137 |
| | | | 398/116 |
| 2015/0088125 | A1 | 3/2015 | Wham |
| 2019/0165572 | A1 * | 5/2019 | Lai ....................... H04L 9/3278 |

FOREIGN PATENT DOCUMENTS

| | | | | | |
|---|---|---|---|---|---|
| CN | 102882604 | A | | 1/2013 | |
| CN | 105450577 | A | | 3/2016 | |
| CN | 206355132 | U | | 7/2017 | |
| CN | 107547002 | A | | 1/2018 | |
| CN | 107681916 | A | | 2/2018 | |
| CN | 109124759 | A | | 1/2019 | |
| CN | 109946216 | A | | 6/2019 | |
| CN | 110071707 | A | | 7/2019 | |
| CN | 110166051 | A | | 8/2019 | |
| CN | 110814146 | A | | 2/2020 | |
| CN | 112540221 | A | * | 3/2021 | ............. G01R 15/04 |
| CN | 112842516 | A | | 5/2021 | |
| CN | 113098448 | A | | 7/2021 | |
| CN | 113616312 | A | | 11/2021 | |
| CN | 113644898 | A | | 11/2021 | |
| CN | 115047786 | A | * | 9/2022 | ............. G05B 17/02 |
| JP | H0787073 | A | | 3/1995 | |
| JP | H08125202 | A | | 5/1996 | |
| JP | 2002335682 | A | | 11/2002 | |
| JP | 2004193918 | A | | 7/2004 | |
| JP | 2005237147 | A | | 9/2005 | |
| JP | 2006135947 | A | | 5/2006 | |
| JP | 2008011595 | A | | 1/2008 | |
| KR | 20010004636 | A | | 1/2001 | |
| KR | 20060011338 | A | * | 2/2006 | .......... H04B 10/693 |
| WO | 2018010659 | A1 | | 1/2018 | |

OTHER PUBLICATIONS

Office action from Japanese Patent Application No. 2024-507042 dated Feb. 4, 2025 and its English translation.
International Search Report in International application No. PCT/CN2022/111840 mailed on Nov. 16, 2022, with English translation provided by WIPO.
Written Opinion of the International Searching Authority in International application No. PCT/CN2022/111840 mailed on Nov. 16, 2022, with English translation provided by WIPO.
Office action from Japanese Patent Application No. 2024-506823 dated on Feb. 4, 2025 and its English translation.
Extended European search report from European Patent Application No. 22855500.9 dated Oct. 14, 2024.
Office action from U.S. Appl. No. 18/681,034 dated May 6, 2025.
Office action and search report from Chinese Patent Application No. 202110921264.0 dated Sep. 8, 2023 and its English translation.
Decision of rejection from Chinese Patent Application No. 202110921264.0 dated Apr. 18, 2024 and its English translation.
Zhao Jiagui, Electronic Circuit Design, 1st ed., pp. 345-346, Apr. 30, 2005, China Metrology Press, and its English translation.
Notification of grant of patent right and search report from Chinese Patent Application No. 202110921262.1 dated Jun. 20, 2024 and its English translation.
Xiong Lan, "An improved adjustable index pulse power generator," Power Supply Technology, Issue 06, Jun. 20, 2013, and its English abstract.
Office action from South Korean Patent Application No. 10-2024-7003945 dated May 26, 2025, and its English translation.
Office action from South Korean Patent Application No. 10-2024-7003923 dated May 26, 2025, and its English translation.
Supplementary European Search Report in the corresponding EP patent Application No. 22855503.3, issued on Oct. 16, 2024.
Office action from corresponding Japanese Patent Application No. 2024-507042 dated Jul. 29, 2025, and its English translation.
Office action from Korean Patent Application No. 10-2024-7003923 dated Dec. 19, 2025, and its English translation.
Office action from European Patent Application No. 22855500.9 dated Feb. 27, 2026.

* cited by examiner

SYNERGISTIC PULSE GENERATION APPARATUS, DEVICE AND METHOD

CROSS-REFERENCE TO RELATED APPLICATIONS

The present application is the U.S. national phase of PCT Application PCT/CN2022/111840 filed on Aug. 11, 2022, which claims priority to Chinese Patent Application No. CN202110921262.1 entitled "Synergistic pulse generation apparatus, system and method and Chinese Patent Application No. CN202110921264.0 entitled "Driving circuit, driving method and pulse generation system", and the above-mentioned patent applications are incorporated herein by reference in their entireties.

TECHNICAL FIELD

The present application relates to the field of pulse generation and medical instruments, and in particular, the present application relates to a synergistic pulse generation apparatus, device and method.

BACKGROUND

A pulse power technique is an electrophysical technique of rapidly compressing energy that is slowly stored and has relatively high density, and converting same or directly releasing same to a load. In recent years, with the constant extension of the use of the pulse power technique into fields such as medical treatment, environmental science, plasma science, food processing, electromagnetic compatibility testing, bioengineering, etc., the requirements for a pulse generator constantly change as well.

An existing pulse generation apparatus has a relatively complex structure, and is generally only capable of generating a pulse signal of a specific width, which cannot meet the complex use requirements for the pulse technique.

SUMMARY

The present application aims to solve at least one aspect of the above technical problems to a certain extent, and provides a synergistic pulse generation apparatus, device and method, which are used for generating pulses in different width ranges and forming more pulse combinations.

In a first aspect, an embodiment of the present application provides a synergistic pulse generation apparatus for generating a pulse signal under the control of a host computer. The synergistic pulse generation apparatus includes:

a driving circuit, which is electrically connected to the host computer, and is configured to receive a first control signal sent by the host computer and convert the first control signal into a first driving signal, and receive a second control signal sent by the host computer and convert the second control signal into a second driving signal; and a pulse generation circuit, which includes a first power supply, a first pulse generation module, which is electrically connected to the first power supply, a second power supply, and a second pulse generation module, which is electrically connected to the second power supply.

The first pulse generation module is configured to store electric energy supplied by the first power supply, and discharge electricity under the control of the first driving signal to form a first pulse signal applied to a load; and the second pulse generation module is configured to store electric energy supplied by the second power supply, and discharge electricity under the control of the second driving signal to form a second pulse signal applied to the load.

The voltage of the second power supply is greater than the voltage of the first power supply, and the width of the second pulse is less than the width of the first pulse.

In a second aspect, an embodiment of the present application provides a synergistic pulse generation device, the synergistic pulse generation device including:

a host computer configured to generate the control signal according to an inputted instruction; and the synergistic pulse generation device according to the first aspect of the present application.

In a third aspect, an embodiment of the present application provides a synergistic pulse generation method, the method being used by the synergistic pulse generation device according to the first aspect of the present application, and including:

a first pulse generation module storing electric energy supplied by a first power supply, and a second pulse generation module storing electric energy supplied by a second power supply;

a driving circuit receiving a first control signal sent by a host computer and converting the first control signal into a first driving signal, and the driving circuit receiving a second control signal sent by the host computer and converting the second control signal into a second driving signal; and a first pulse generation module receiving the first driving signal and discharging electricity under the control of the first driving signal to form a first pulse signal applied to a load, and a second pulse generation module receiving the second driving signal and discharging electricity under the control of the second driving signal to form a second pulse signal applied to the load.

The voltage of the second power supply is greater than the voltage of the first power supply, and the width of the second pulse signal is less than the width of the first pulse signal.

The beneficial technical effects brought about by the technical solutions provided in the embodiments of the present application are as follows:

by means of the synergistic pulse generation apparatus, device and method provided in the embodiments of the present application, a driving circuit respectively converts a first control signal and a second control signal, which are sent by a host computer, into a first driving signal and a second driving signal, and a pulse generation circuit can selectively form a first pulse signal and/or a second pulse signal of different widths according to the first driving signal and the second driving signal, so as to achieve the purpose of applying a composite pulse signal to a load. Taking the load being tumor cells as an example, the action of a composite pulse is conducive to an improvement in the ablation effect on the tumor cells.

Additional aspects and advantages of the present application will be set forth in part in the following description, which will become apparent from the following description, or may be learned by practice of the present application.

BRIEF DESCRIPTION OF THE DRAWINGS

The above and/or additional aspects and advantages of the present application will become apparent and easily comprehensible from the following description of embodiments in below in conjunction with drawings.

Figure 1:
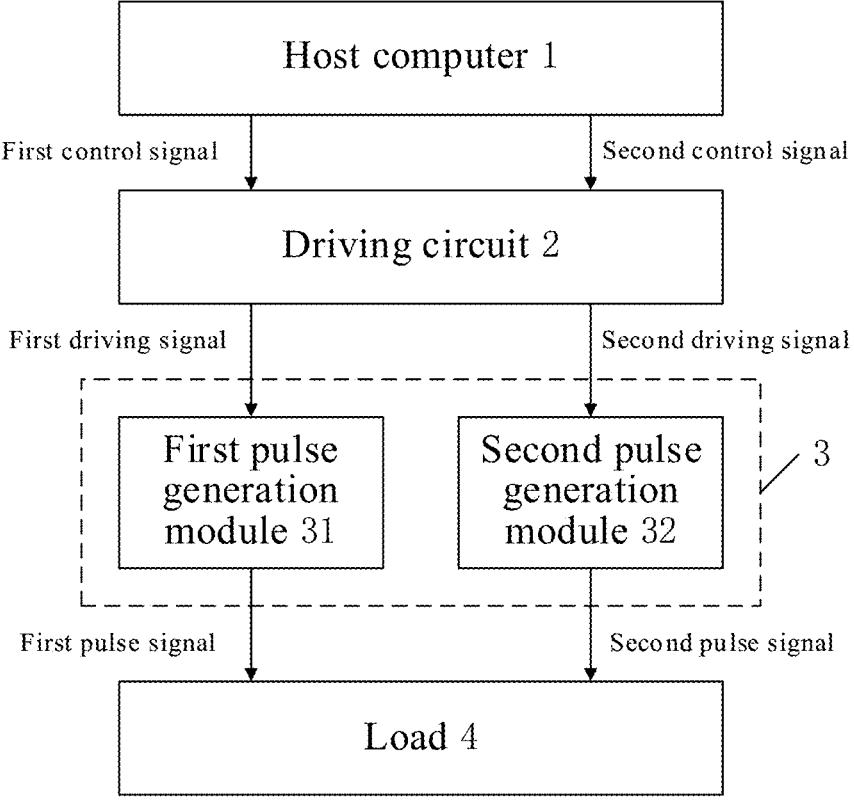
Figure 2:
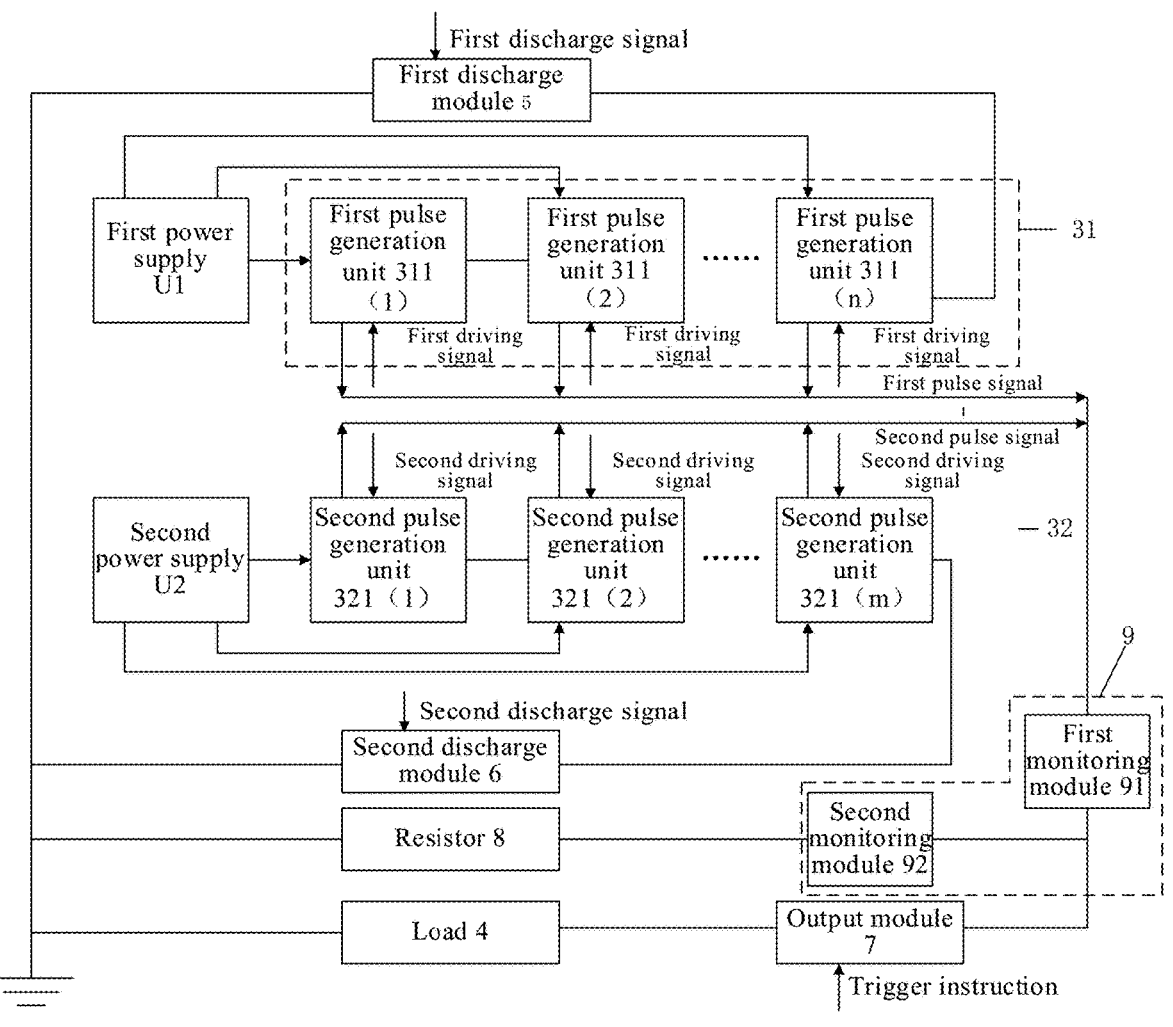
Figure 3:
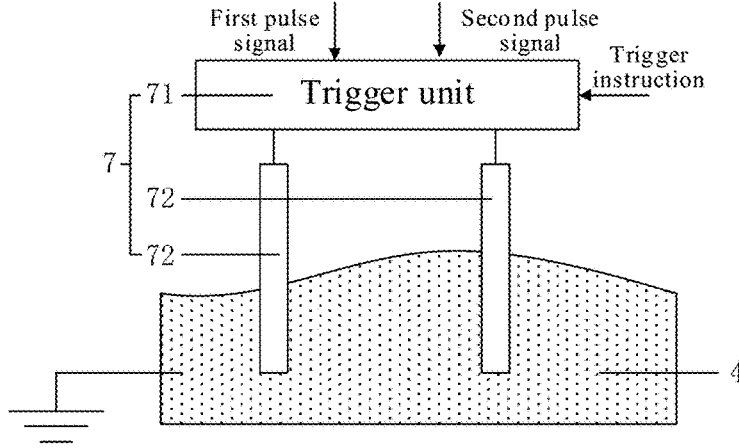
Figure 4:
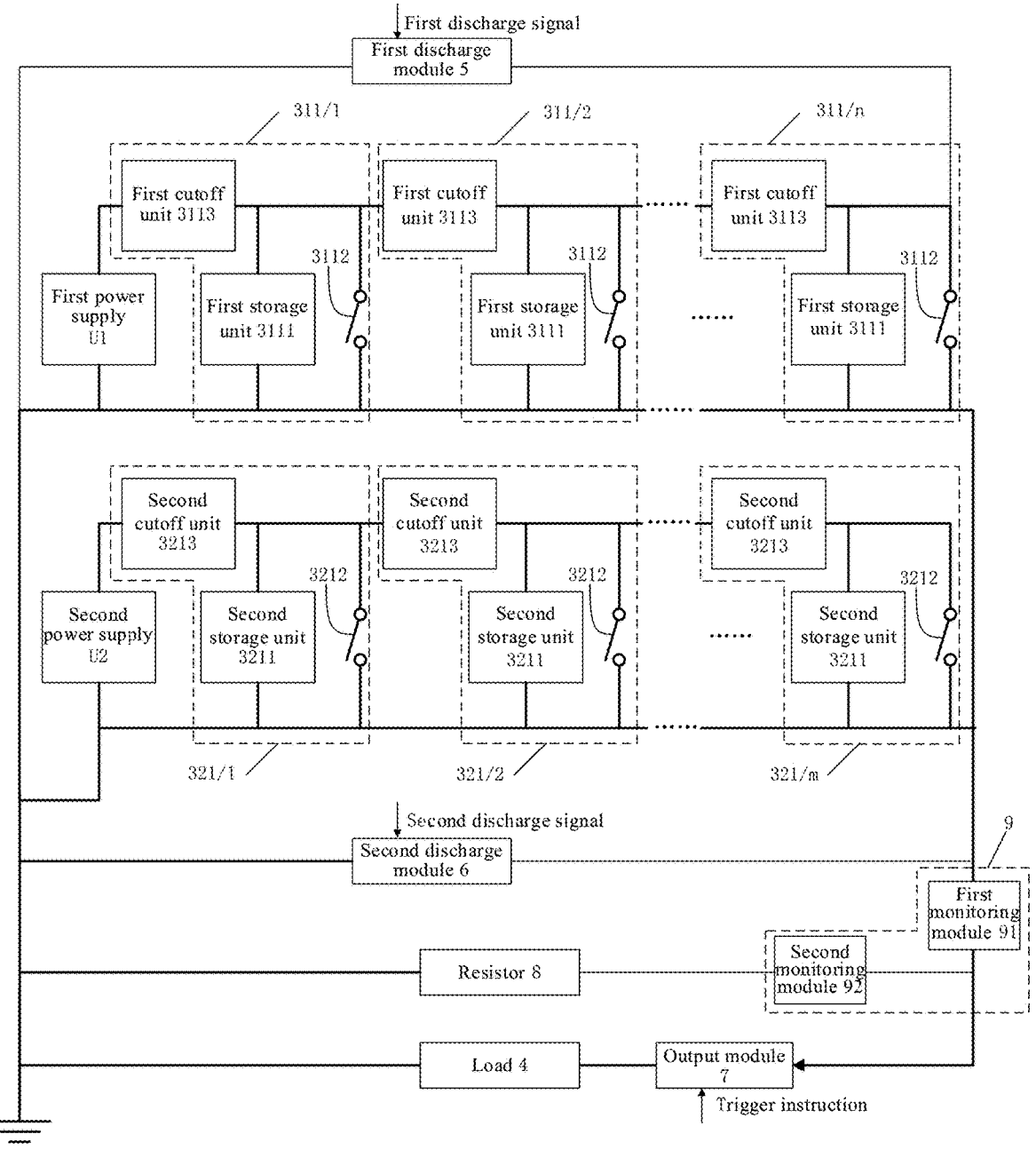
Figure 5:
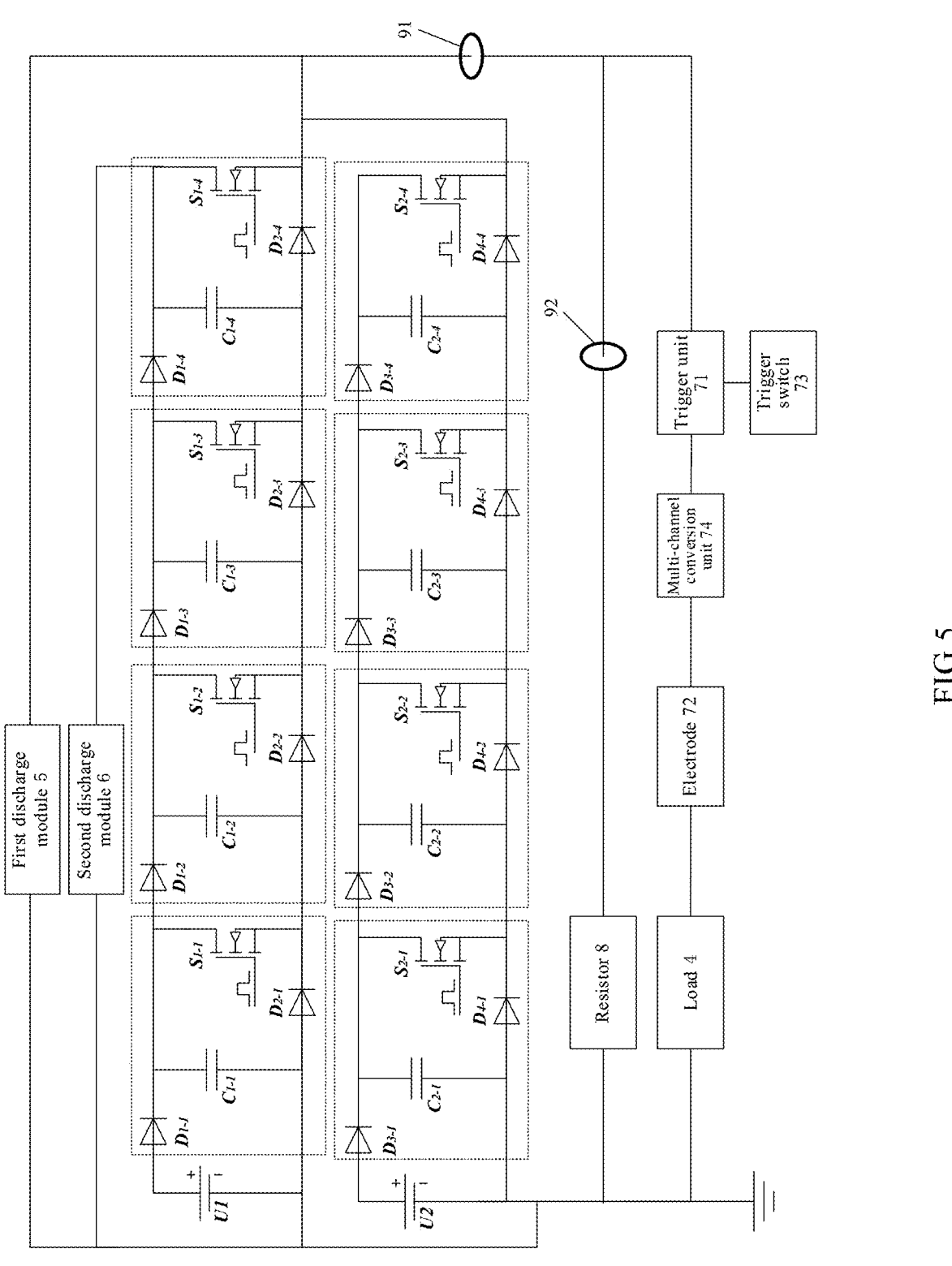
Figure 6:
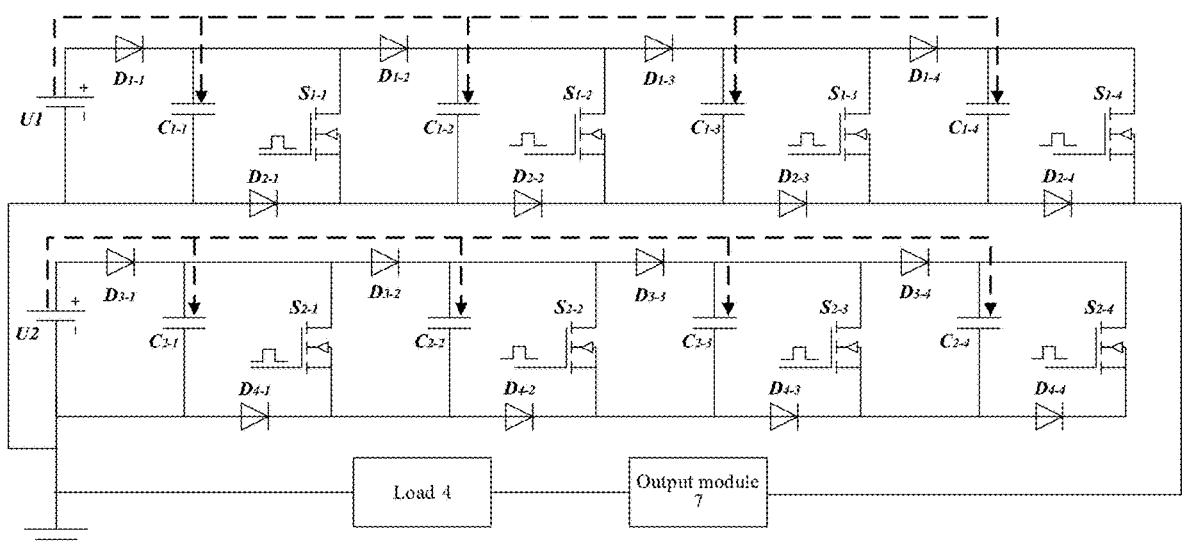
Figure 7:
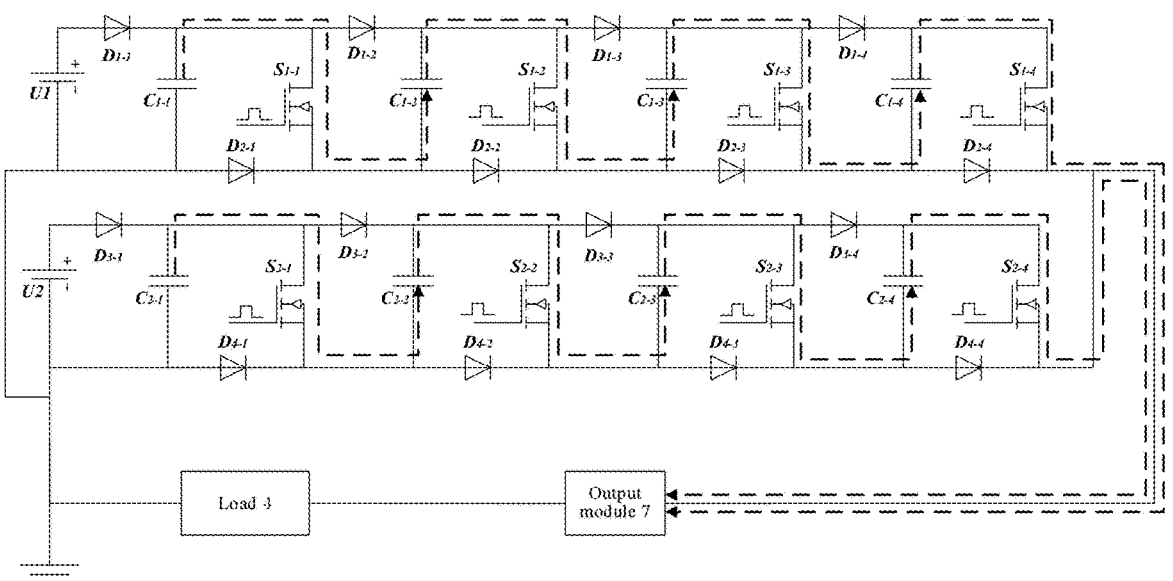
Figure 8:
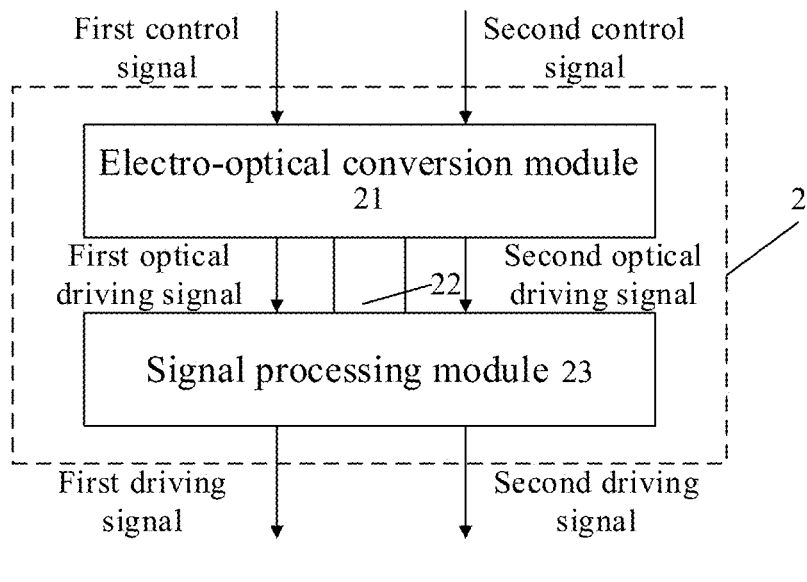
Figure 9:
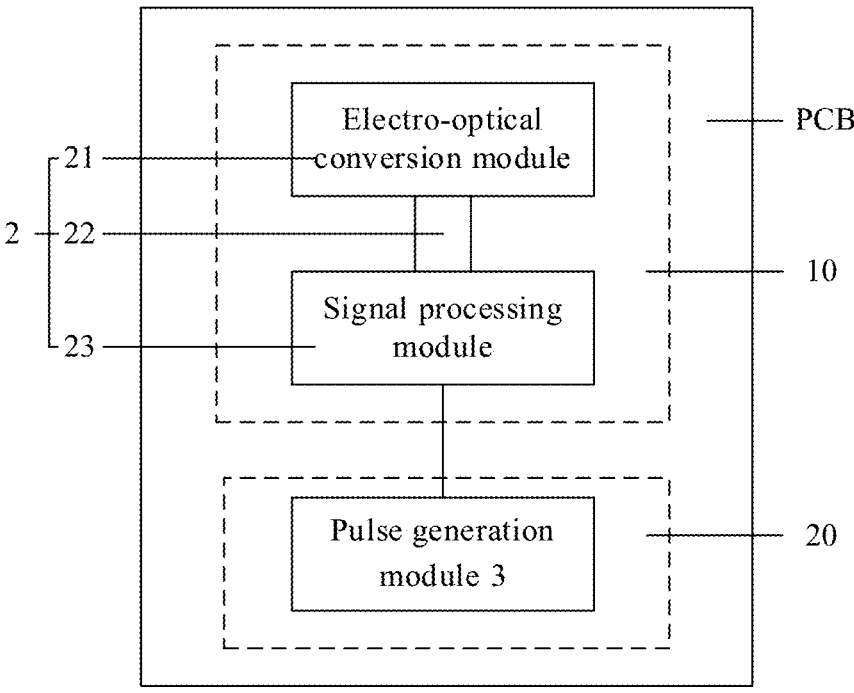
Figure 10:
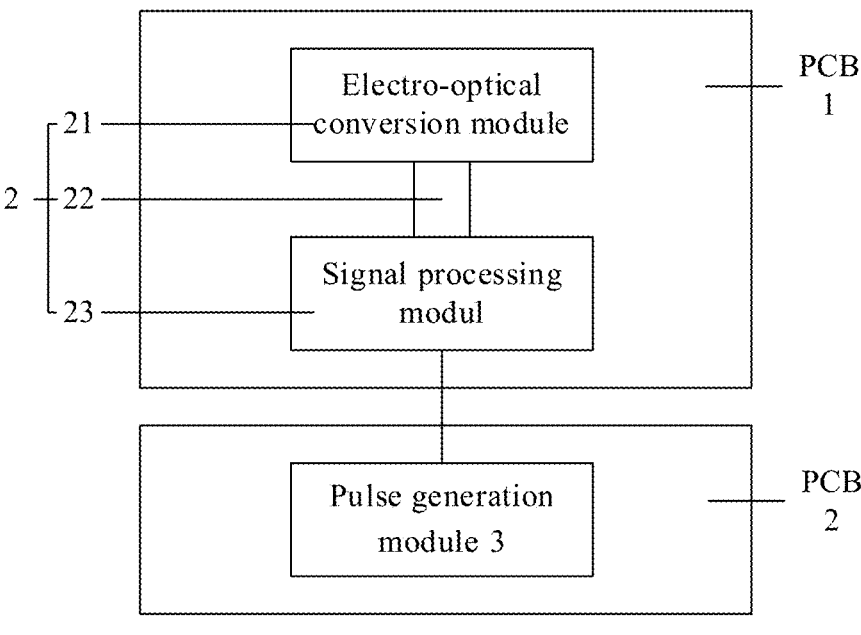
Figure 11:
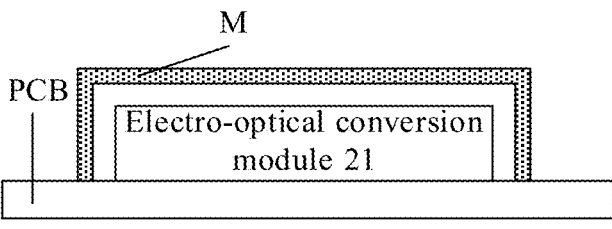
Figure 12:
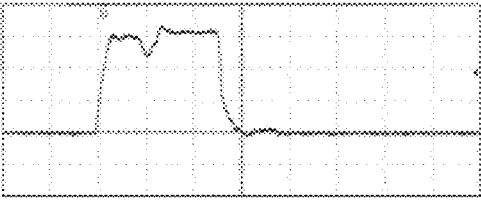
Figure 13:
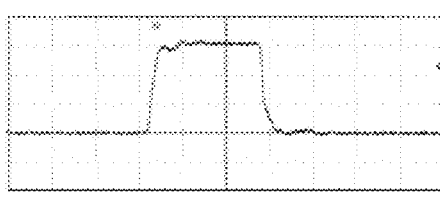
Figure 14:
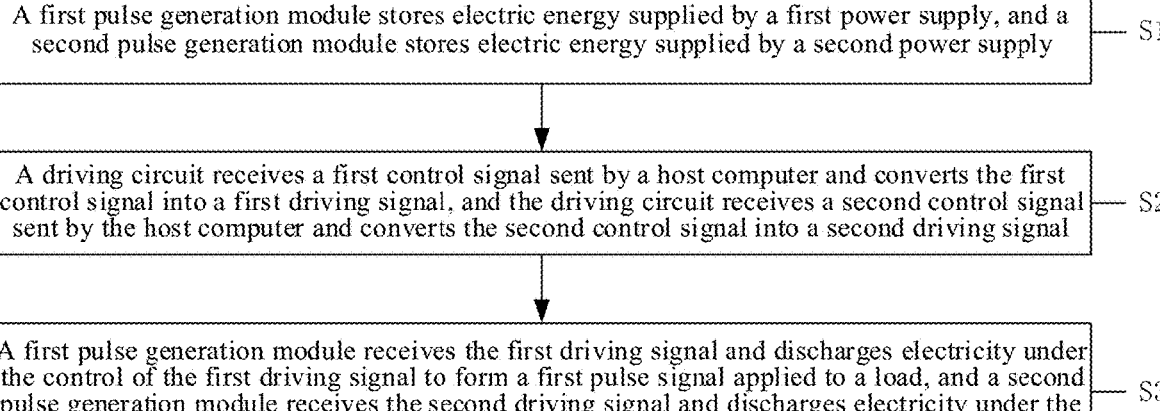
Figure 15:
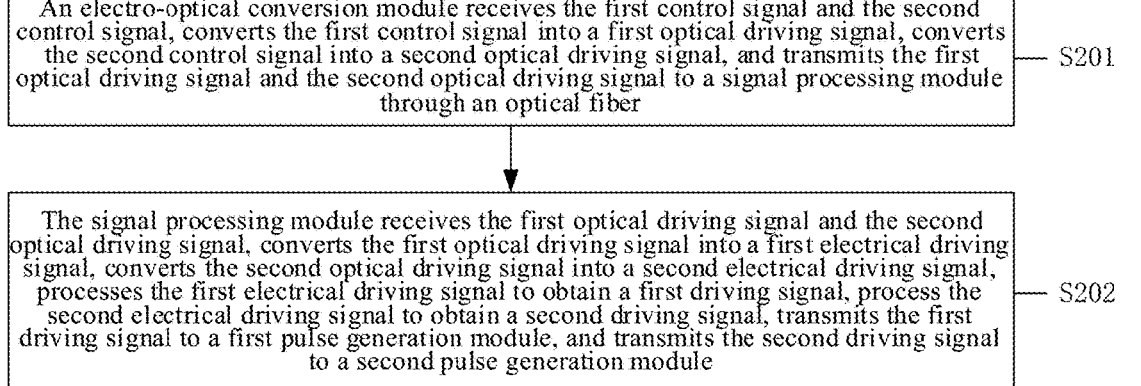
Figure 16:
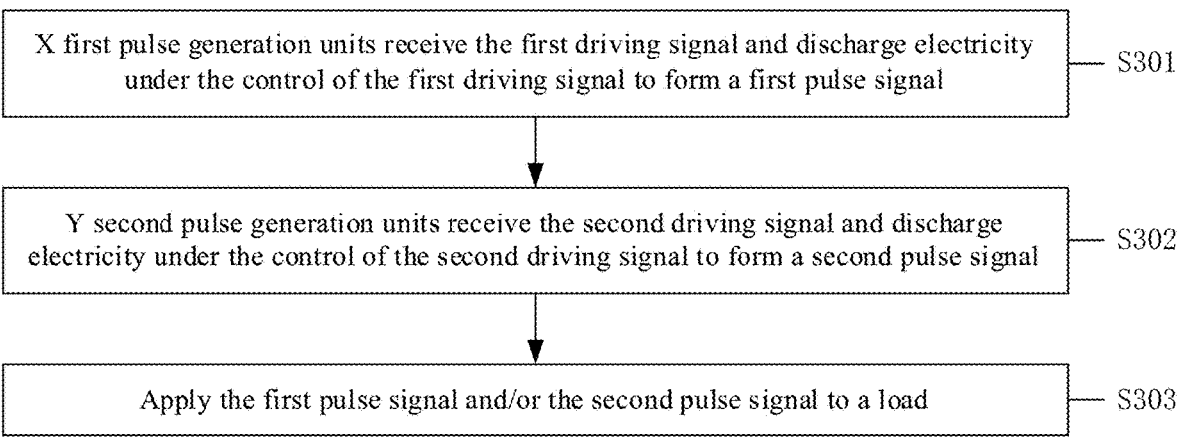
Figure 17:
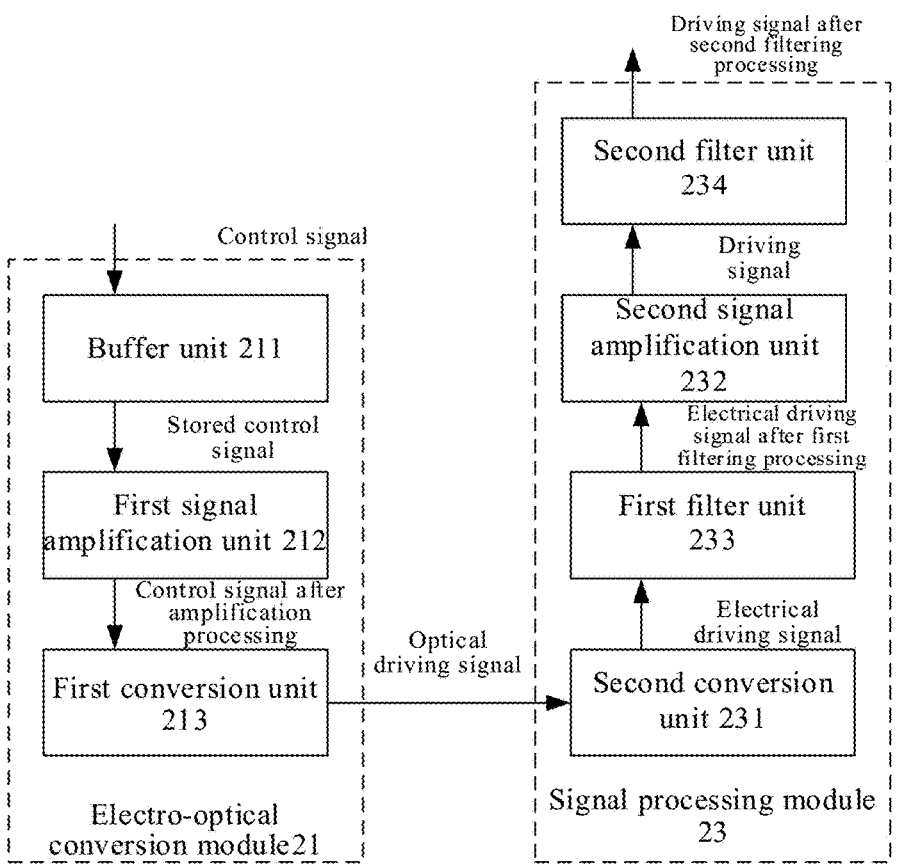
Figure 18:
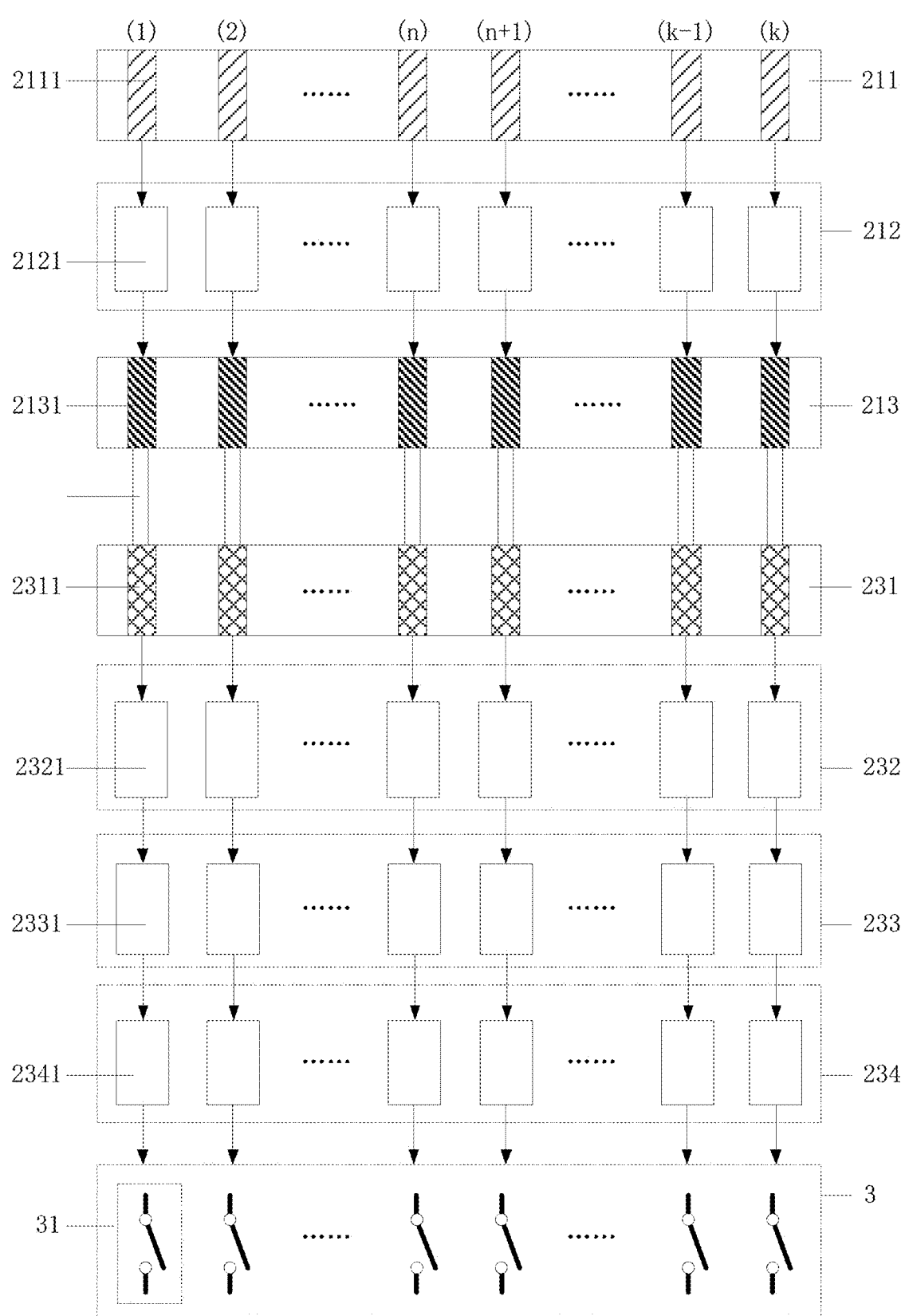

FIG. 1 is a schematic diagram of the connection between the synergistic pulse generation apparatus provided in an embodiment of the present application and a host computer and the connection between the synergistic pulse generation apparatus and a load;

FIG. 2 is a schematic structural diagram of another pulse generation circuit in a synergistic pulse generation apparatus provided in an embodiment of the present application;

FIG. 3 is a schematic diagram of the contact between an output module and a load as provided in an embodiment of the present application;

FIG. 4 is a schematic structural diagram of still another pulse generation circuit in a synergistic pulse generation apparatus provided in an embodiment of the present application;

FIG. 5 is a schematic structural diagram of yet another pulse generation circuit in a synergistic pulse generation apparatus provided in an embodiment of the present application;

FIG. 6 is a schematic diagram of the current of the pulse generation circuit as shown in FIG. 5 in a charging state;

FIG. 7 is a schematic diagram of the current of the pulse generation circuit as shown in FIG. 5 in a discharging state;

FIG. 8 is a schematic structural diagram of a driving circuit in a synergistic pulse generation apparatus provided in an embodiment of the present application;

FIG. 9 is a schematic diagram of the distribution of a synergistic pulse generation apparatus provided in an embodiment of the present application on a circuit board;

FIG. 10 is a schematic diagram of the distribution of another synergistic pulse generation apparatus provided in an embodiment of the present application on a circuit board;

FIG. 11 is a schematic structural diagram of a synergistic pulse generation apparatus having a shielding structure as provided in an embodiment of the present application;

FIG. 12 is a schematic diagram of a pulse signal generated when no shielding structure is arranged in the prior art;

FIG. 13 is a schematic diagram of a pulse signal generated after a shielding structure is arranged as provided in an embodiment of the present application;

FIG. 14 is a schematic diagram of a flow of a synergistic pulse generation method provided in an embodiment of the present application;

FIG. 15 is a schematic diagram of a flow of step S2 in a synergistic pulse generation method provided in an embodiment of the present application;

FIG. 16 is a schematic diagram of a flow of step S3 in a synergistic pulse generation method provided in an embodiment of the present application;

FIG. 17 is a schematic structural diagram of a driving circuit provided in an embodiment of the present application; and FIG. 18 is a schematic structural diagram of another driving circuit provided in an embodiment of the present application.

LIST OF REFERENCE NUMERALS

1—Host computer; 2—Driving circuit; 21—Electro-optical conversion module; 22—Optical fiber; 23—Signal processing module; 3—Pulse generation circuit; 31—First pulse generation module; 311—First pulse generation unit; 3111—First storage unit; 3112—First switch unit; 3113—First cutoff unit; 32—Second pulse generation module; 321—Second pulse generation unit; 3211—Second storage unit; 3212—Second switch unit; 3213—Second cutoff unit; 4—Load; 5—First discharge module; 6—Second discharge module; 7—Output module; 71—Trigger unit; 72—Electrode; 73—Trigger switch; 74—Multi-channel conversion unit; 8—Resistor; 9—Monitoring module; 91—First monitoring unit; 92—Second monitoring unit; U1—First power supply; U2—Second power supply; M—Shielding structure; PCB—Circuit board; 10—First portion; 20—Second portion; PCB1—First circuit board; and PCB2—Second circuit board.

DETAILED DESCRIPTION

The present application will be described in detail below. Examples of the embodiments of the present application are shown in the drawings, and throughout the drawings, the same or similar reference signs refer to the same or similar components or components having the same or similar functions. In addition, the detailed description of known techniques will be omitted if unnecessary to the shown features of the present application. The embodiments described below with reference to the drawings are exemplary and are merely used to be illustrative of the present application, but should not be construed as limiting the present application.

It should be understood by the skilled in the art that, unless otherwise defined, all terms (including technical and scientific terms) used herein have the same meaning as commonly understood by those of ordinary skills in the art. It should also be understood that terms, such as those defined in commonly used dictionaries, should be construed as having meanings that are consistent with their meanings in the context of the prior art, and will not be construed in an idealized or overly formal sense unless specifically defined as here.

It should be understood by the skilled in the art that, as used herein, the singular form "a", "an" or "the" may include plural forms as well, unless otherwise stated. It should be further understood that the term "include" used in the specification of the present application specifies the presence of the features, integers, steps, operations, elements and/or components, but does not exclude the presence or addition of one or more of other features, integers, steps, operations, elements, components and/or their combinations.

In recent years, with the constant extension of the use of the pulse power technique into fields such as medical treatment, environmental science, plasma science, food processing, electromagnetic compatibility testing, bioengineering, etc., the requirements for a pulse generator constantly change as well.

Taking the field of medicines as an example, the inventors of the present application have found that, when tumor cell ablation is performed using an electroablation technique, a better ablation effect can be achieved by the composite use of multiple types of pulses having different widths than the use of a single type of pulse in some cases. For example, when a microsecond pulse is applied to tumor cells, although the ablation area is relatively large, the ablation rate for the tumor cell, and particularly for a malignant tumor cell having a relatively large aberration, is relatively low; and when a nanosecond pulse is applied to the tumor cells, although the ablation rate is relatively high, the ablation area is relatively small. The ablation effect on the tumor cells can be significantly improved by the composite use of the microsecond pulse and the nanosecond pulse. In addition to performing ablation of tumor cells using reversible electroporation induced by the nanosecond pulse, it is also possible to further synergistically apply a microsecond or millisecond pulse during an existence duration of irreversible electroporation induced by the nanosecond pulse, so that an electric field of the microsecond or millisecond pulse penetrates to reach the interiors of cells using pores of cell membranes, further inducing cell apoptosis, whereby a better ablation effect is achieved than separately using the nanosecond pulse, the microsecond pulse or the millisecond pulse.

To generate a composite pulse, a corresponding pulse generation apparatus is required. However, a traditional pulse generation apparatus has a relatively complex structure, and is generally only capable of generating a pulse signal of a specific width, which cannot meet the complex use requirements for the pulse.

The synergistic pulse generation apparatus, device and method provided by the present application aim to solve at least one aspect of the above technical problems to a certain extent.

The technical solution of the present application, and how the technical solution of the present application solves the above technical problems will be described below in details with particular embodiments.

An embodiment of the present application provides a synergistic pulse generation apparatus, and the synergistic pulse generation apparatus may be configured to generate a pulse signal according to a control signal under the control of a host computer 1. For case of description, a signal outputted by the synergistic pulse generation apparatus is also referred to as a synergistic pulse or a composite pulse. As shown in FIG. 1, the synergistic pulse generation apparatus provided in the embodiment includes a driving circuit 2 and a pulse generation circuit 3, which is electrically connected to the driving circuit 2, the driving circuit 2 being electrically connected to the host computer 1.

The driving circuit 2 is electrically connected to the host computer 1, and is configured to receive a first control signal sent by the host computer 1 and convert the first control signal into a first driving signal, and receive a second control signal sent by the host computer 1 and convert the second control signal into a second driving signal.

The pulse generation circuit 3 includes a first power supply, a first pulse generation module 31, which is electrically connected to the first power supply, a second power supply, and a second pulse generation module 32, which is electrically connected to the second power supply. The first pulse generation module 31 is configured to store electric energy supplied by first power supply, and discharge electricity under the control of the first driving signal to form a first pulse signal applied to a load. The second pulse generation module 32 is configured to store electric energy supplied by the second power supply, and discharge electricity under the control of the second driving signal to form a second pulse signal applied to the load. In some embodiments, the voltage of the second power supply is greater than the voltage of the first power supply, the width of the second pulse is smaller than the width of the first pulse, and the time when the second pulse generation module 32 receives the second driving signal is different from the time when the first pulse generation module 31 receives the first driving signal.

It should be noted that the time when the second pulse generation module 32 receives the second driving signal being different from the time when the first pulse generation module 31 receives the first driving signal means that the first pulse generation module 31 does not receive the first driving signal when the second pulse generation module 32 receives the second driving signal, and the second pulse generation module 32 does not receive the second driving signal when the first pulse generation module 31 receives the first driving signal, that is, the first pulse signal and the second pulse signal do not form at the same time, so as to avoid the first pulse signal and the second pulse signal from interfering with each other.

By means of the synergistic pulse generation apparatus provided in the embodiment, a driving circuit 2 respectively converts a first control signal and a second control signal, which are sent by a host computer 1, into a first driving signal and a second driving signal, and a pulse generation circuit 3 can selectively form a first pulse signal and/or a second pulse signal of different widths according to the first driving signal and the second driving signal, so as to achieve the purpose of applying a composite pulse signal to a load 4. Taking the load 4 being tumor cells as an example, the action of a composite pulse is conducive to an improvement in the ablation effect on the tumor cells. The first pulse signal may be configured to be a microsecond pulse signal or a millisecond pulse signal, and the second pulse signal may be configured to be a nanosecond pulse signal.

In some optional embodiments, as shown in FIG. 2, in the synergistic pulse generation apparatus, the pulse generation circuit 3 includes a first discharge module 5 and a second discharge module 6. The first discharge module 5 is electrically connected to the first pulse generation module 31 and the ground, respectively, and is configured to connect the first pulse generation module 31 to the ground under the control of a first discharge signal to release residual electricity in the first pulse generation module 31. The second discharge module 6 is electrically connected to the second pulse generation module 32 and the ground, respectively, and is configured to connect the second pulse generation module 32 to the ground under the control of a second discharge signal to release residual electricity in the second pulse generation module 32.

In a particular embodiment, as shown in FIG. 2, the first discharge module 5 is a first relay, and the second discharge module 6 is a second relay. The first relay is switched on when receiving the first discharge signal, so that the first pulse generation module 31 is connected to the ground, and the residual electricity in the first pulse generation module 31 is thus released to the ground. Similarly, the residual electricity in the second pulse generation module 32 can also be released to the ground. Based on this, by means of the first discharge signal and the second discharge signal, the relay may be switched on by means of manual trigger, and the relay may also be switched on by means of an electrical signal, etc. Alternatively, the discharge module may also use other devices that can function as a switch, for example, a transistor, a button switch, etc.

Specifically, as shown in FIG. 2, a discharge operation is usually conducted when the synergistic pulse generation apparatus stops operating, so as to avoid an adverse effect caused by residual electricity in the synergistic pulse generation circuit 3 upon next time of startup, and also avoid an electric shock within a time period when the synergistic pulse generation circuit 3 is switched off. Certainly, it is also possible to conduct the discharge operation upon the startup of the synergistic pulse generation apparatus, so as to further avoid an adverse effect caused by residual electricity in a synergistic pulse generator upon the startup.

In some optional embodiments, as shown in FIG. 2, in the synergistic pulse generation apparatus, the synergistic pulse generation circuit 3 further includes an output module 7. The output module 7 is electrically connected to the first pulse generation module 31 and the second pulse generation module 32, respectively, and is configured to apply the first pulse signal and/or the second pulse signal to the load 4 under the control of the trigger instruction. Specifically, when the synergistic pulse generation circuit 3 in the present embodiment is applied in medical treatment and biological experiments, the load 4 may be a certain site of a living body, for example, a cancerous site of a patient with cancer, and may also be an in vitro organization, an organ, a cell population, etc. In the synergistic pulse generation apparatus in the present embodiment, the application of the first pulse signal and/or the second pulse signal to the load 4 is controlled by means of the output module 7, so as to realize the controllability of the action of pulses on the load 4, improving the pulse action effect.

Optionally, as shown in FIG. 3, in the synergistic pulse generation apparatus in the present embodiment, the output module 7 includes a trigger unit 71 and at least a pair of electrodes 72 electrically connected to the trigger unit 71. The trigger unit 71 is electrically connected to the first pulse generation module 31 and the second pulse generation module 32, respectively, and the electrodes 72 are used for being in contact with the load 4. The trigger unit 71 is configured to switch on when being triggered by a trigger instruction, so that the first pulse signal and/or the second pulse signal are transmitted to the electrodes 72.

Optionally, as shown in FIG. 5, the output module 7 further includes a trigger switch 73 associated with the trigger unit 71. Specifically, when the synergistic pulse generation circuit 3 in the present embodiment is applied in a medical instrument, e.g., an electroablation device, the trigger switch 73 may be a foot switch, and the trigger unit 71 may be a relay. When the foot switch is triggered, the trigger action serves as the trigger instruction so that the trigger unit 71 (i.e., the relay) is triggered by the trigger instruction to switch on, and thus the first pulse signal and/or the second pulse signal are outputted to the electrode 72 to act on the load 4 that is in contact with the electrode 72.

Optionally, as shown in FIG. 5, the output module 7 further include a multi-channel conversion unit 74. The multi-channel conversion unit 74 may convert one channel of a signal into multiple channels of signals, and each pair of electrodes 72 need two channels of identical signals. The multi-channel conversion unit 7 may be configured to be expandable. For example, under a certain usage condition, one pair of electrodes 72 is required, however, in some other cases, a four-channel, six-channel or even multi-channel conversion unit 74 may be used so that signal requirements of multiple pairs of electrodes 72 can be met when the use of the multiple pairs of electrodes is required.

In some optional embodiments, as shown in FIG. 2, in the synergistic pulse generation apparatus, the synergistic pulse generation circuit 3 further includes a resistor 8 and a monitoring module 9. The resistor 8 is electrically connected to the first pulse generation module 31, the second pulse generation module 32 and the ground, respectively, and the first pulse signal and/or the second pulse signal are also applied to the resistor 8. The monitoring module 9 includes a first monitoring unit 91 and a second monitoring unit 92. The first monitoring unit 91 is configured to monitor currents outputted by the first pulse signal and/or the second pulse signal. The second monitoring unit 92 is configured to monitor voltages applied to the resistor 8 by the first pulse signal and/or the second pulse signal.

Certainly, it is also possible to use one of the monitoring units to monitor one of a voltage or a current outputted by a synergistic pulse signal. For example, only the first monitoring unit 91 is used, and at this time, the first monitoring unit 91 may be configured to be a voltage sensor or a current sensor.

Specifically, as shown in FIG. 2, the first monitoring unit 91 is electrically connected to the first pulse generation module 31 and the second pulse generation module 32, respectively, and the second monitoring unit 92 is also electrically connected to the first pulse generation module 31 and the second pulse generation module 32, respectively. A branch circuit in which the resistor 8 is located and a branch circuit in which the load 4 is located are connected in parallel, and therefore, the resistor 8 and the load 4 receive the same pulse signal at the same time. Furthermore, the monitoring module 9 also synchronously performs monitoring on the voltages applied to the resistor 8 by the first pulse signal and/or the second pulse signal and on the currents outputted by the first pulse signal and/or the second pulse signal.

Optionally, as shown in FIG. 5, the first monitoring unit 91 includes a first Pearson coil, and the second monitoring unit 92 includes a second Pearson coil. The first Pearson coil is configured to sense the currents outputted by the first pulse signal and/or the second pulse signal, and the second Pearson coil is configured to sense the voltages applied to the resistor 8 by the first pulse signal and/or the second pulse signal, thereby realizing monitoring of the currents and voltages outputted by the first pulse signal and/or the second pulse signal.

In a particular embodiment, a first pulse signal and a second pulse signal having certain parameters are formed, and the pulses have corresponding currents and voltages when applied to the resistor 8. The two Pearson coils above can also sense the corresponding currents and voltages. When sensing results of the two Pearson coils above conform to the parameters of the first pulse signal and the second pulse signal, then it is determined that the synergistic pulse generation circuit 3 at this time is in a normal operation state; and once the sensing results of the two Pearson coils above deviate from the parameters of the first pulse signal and the second pulse signal, then it is determined that the synergistic pulse generation apparatus is in an abnormal operation state. In this way, an operator can find a fault and take corresponding measures in a timely manner.

For example, when the synergistic pulse generation circuit 3 in the present embodiment is applied to the field of medicines, i.e., a pulse therapy instrument, whether or not a first pulse and/or a second pulse that are/is outputted are/is normal can be determined in a timely manner according to the monitoring result provided by the monitoring module 9, thereby ensuring that an output on the load 4 coordinates with a set output parameter.

Specifically, as shown in FIG. 2, in the synergistic pulse generation apparatus provided by the embodiment, the pulse generation circuit 3 includes a first power supply U1, a first pulse generation module 31, which is electrically connected to the first power supply U1, a second power supply U2, and a second pulse generation module 32, which is electrically connected to the second power supply U2.

As shown in FIG. 2, the first pulse generation module 31 includes n stages of first pulse generation units 311. The first pulse generation units 311 are configured to receive electric energy supplied by the first power supply U1 and store same, and release stored electric energy when receiving a first control signal. X first pulse generation units 311 receiving the first control signal discharge electricity to form the first pulse signal applied to the load 4, where n is an integer greater than or equal to 1, and x is an integer greater than or equal to 1 and less than or equal to n.

As shown in FIG. 2, the second pulse generation module 32 includes m stages of second pulse generation units 321. The second pulse generation units 321 are configured to receive electric energy supplied by the second power supply U2 and store same, and release stored electric energy when receiving a second driving signal. Y second pulse generation units 321 receiving the second control signal discharge electricity to form the second pulse signal applied to the load 4, where m is an integer greater than or equal to 1, and y is an integer greater than or equal to 1 and less than or equal to m.

For case of illustration, in subsequent embodiments, the voltage of the first power supply U1 is referred to as a first voltage, and the voltage of the second power supply U2 is referred to as a second voltage.

It should be noted that, as shown in FIG. 2, theoretically, all the x first pulse generation units 311 receiving the first driving signal discharge electricity with the first voltage, but actually, due to the influence of factors such as equivalent impedance of various devices in the pulse generation circuit 3, the discharge voltage of the first pulse generation unit 311 is slightly lower than the first voltage. However, the difference between the actual discharge voltage of the first pulse generation unit 311 and the first voltage is usually very small, and therefore, during a discharge process of the first pulse generation module 31, the voltage of the first pulse signal applied to the load 4 may be approximated as x times of the first voltage. Similarly, during a discharge process of the second pulse generation module 32, the voltage of the second pulse signal applied to the load 4 may be approximated as y times of the second voltage. For case of illustration, in subsequent embodiments, the actual voltage values of the first pulse generation units 311 and the second pulse generation units 321 during discharge will not be explained and illustrated to describe the first voltage and the second voltage. Based on the above description, the number of first pulse generation units 311 discharging electricity at the same time and the number of second pulse generation units 321 discharging electricity at the same time are set, such that the voltage of the first pulse signal and the voltage of the second pulse signal can be adjusted. In a specific implementation, more accurate adjustment of the voltage of a generated pulse signal can be realized by considering the relationship between a power voltage and an actual discharge voltage.

Different pulse combinations can be formed by means of setting the first driving signal and the second driving signal in different manners. For example, in a particular embodiment, a pulse combination includes a plurality of first pulse groups, the time interval between two adjacent first pulse groups is t1, each of the first pulse groups includes a first pulse signals, and the time interval between two adjacent first pulse signals is t2. In another particular embodiment, the pulse combination includes a plurality of second pulse groups, the time interval between two adjacent second pulse groups is t3, each of the second pulse groups includes b second pulse signals, and the time interval between two adjacent second pulse signals is t4. In still another particular embodiment, the pulse combination includes a plurality of first pulse signals and a plurality of second pulse signals. It is possible to alternately apply the first pulse signals and the second pulse signals to the load 4. It is also possible to apply the second pulse signals to the load 4 after all the first pulse signals have been applied to the load 4, or apply the second pulse signals to the load 4 after all the second pulse signals have been applied to the load 4. It is also possible to combine these first pulse signals into a plurality of first pulse groups and combine these second pulse signals into a plurality of second pulse groups, and alternately apply the first pulse groups and the second pulse groups to the load 4.

In the plurality of embodiments above, the optional framework of the pulse generation circuit 2 in the synergistic pulse generation apparatus is illustrated. In the following embodiments, the structures of the stages of the first pulse generation unit 311 and the connection relationship between the stages of the first pulse generation units 311 in the first pulse generation module 31, and the structures of the stages of the second pulse generation unit 321 and the connection relationship between the stages of the second pulse generation units 321 in the second pulse generation module 32 will be illustrated in details.

In an optional embodiment, as shown in FIG. 4, in the synergistic pulse generation circuit 3, the first pulse generation units 311 each include a first storage unit 3111, a first switch unit 3112 and a first cutoff unit 3113, and the second pulse generation units 321 each include a second storage unit 3211, a second switch unit 3212 and a second cutoff unit 3213.

As shown in FIG. 4, the first switch units 3112 are configured to switch on under the control of the first driving signal so that the respective first storage units 3111 at the same stages as those of the first switch units 3112 receiving the first driving signal are connected in series and discharge electricity to form first pulse signals; and the first cutoff unit 3113 is configured to only allow a current to flow from the first power supply U1 to the first pulse generation unit 311, or flow from the current stage of the first pulse generation unit 311 to the next stage of a first pulse generation unit 311.

As shown in FIG. 4, the second switch units 3212 are configured to switch on under the control of the second driving signal so that the respective second storage units 3211 at the same stages as those of the second switch units 3212 receiving the second driving signal are connected in series and discharge electricity to form second pulse signals; and the second cutoff units 3213 is configured to only allow a current to flow from the second power supply U1 to the second pulse generation unit 321, or flow from the current stage of the second pulse generation unit 321 to the next stage of a second pulse generation unit 321.

Furthermore, as shown in FIG. 4, two ends of each stage of the first storage unit 3111 are electrically connected to two ends of the first power supply U1, respectively, a control end of each stage of the first switch unit 3112 is configured to receive the first driving signal, and a first end and a second end of each stage of the first switch unit 3112 are electrically connected to a first end of the current stage of the first storage unit 3111 and a second end of the next stage of the first storage unit 3111, respectively; and two ends of each stage of the second storage unit 3211 are electrically connected to two ends of the second power supply U1, respectively, a control end of each stage of the second switch unit 3212 is configured to receive the second driving signal, and a first end and a second end of each stage of the second switch are electrically connected to a first end of the current stage of the second storage unit 3111 and a second end of the next stage of the second storage unit 3211, respectively.

In some embodiments, the first storage unit 3111 includes a first capacitor, and the second storage unit 3211 includes a second capacitor. The first switch unit 3112 includes a first solid-state switch device, and the second switch unit 3212 includes a second solid-state switch. The first cutoff unit 3113 includes a first cutoff device and a second cutoff device, and the second cutoff unit 3213 includes a third cutoff device and a fourth cutoff device. The first cutoff device includes a first diode, the second cutoff device includes a second diode, the third cutoff device includes a third diode, and the fourth cutoff device includes a fourth diode. That is, the capacitors are used as the storage units, the solid-state switch devices are used as the switch units, and the diodes are used as the cutoff devices. The solid-state switch devices may be implemented by a metal-oxide-semiconductor field-effect transistor (MOSFET), an insulated gate bipolar transistor (IGBT) or a crystal triode, etc.

As shown in FIG. 5, in the pulse generation circuit 3, the first pulse generation module 31 includes four stages of the first pulse generation units 311, and the second pulse generation module 32 includes four stages of the second pulse generation units 321, that is, n and m are both equal to 4. It should be noted that this is for an illustrative purpose only, and is not used for limiting the number of stages of the first pulse generation units 311 in the first pulse generation module 31 and the number of stages of the second pulse generation units 321 in the second pulse generation module 32.

Referring to FIG. 5, the first to fourth stages of the first switch units 3112, i.e., the first to fourth stages of first solid-state switch device, are respectively a solid-state switch device $S_{1-1}$, a solid-state switch device $S_{1-2}$, a solid-state switch device $S_{1-3}$ and a solid-state switch device $S_{1-4}$. The first to fourth stages of the first storage units are respectively a capacitor $C_{1-1}$, a capacitor $C_{1-2}$, a capacitor $C_{1-3}$ and a capacitor $C_{1-4}$. The first to fourth stages of the first cutoff devices are respectively a diode $D_{1-1}$, a diode $D_{1-2}$, a diode $D_{1-3}$ and a diode $D_{1-4}$. The first to fourth stages of the second cutoff devices are respectively a diode $D_{2-1}$, a diode $D_{2-2}$, a diode $D_{2-3}$ and a diode $D_{2-4}$.

As shown in FIG. 5, the first to fourth stages of the second switch units 3212, i.e., the first to fourth stages of the second solid-stage switch devices, are respectively a solid-state switch device $S_{2-1}$, a solid-state switch device $S_{2-2}$, a solid-state switch device $S_{2-3}$ and a solid-state switch device $s_{2-4}$. The first to fourth stages of the second storage units 3211 are respectively a capacitor $C_{2-1}$, a capacitor $C_{2-2}$, a capacitor $C_{2-3}$ and a capacitor $C_{2-4}$. The first to fourth stages of the third cutoff devices are respectively a diode $D_{3-1}$, a diode $D_{3-2}$, a diode $D_{3-3}$ and a diode $D_{3-4}$. The first to fourth stages of the fourth cutoff devices are respectively a diode $D_{4-1}$, a diode $D_{4-2}$, a diode $D_{4-3}$ and a diode $D_{4-4}$.

Referring to FIG. 6, the first power supply U1 and the second power supply U2 are both voltage sources. When the solid-state switch device $S_{1-1}$, the solid-state switch device $S_{1-2}$, the solid-state switch device $S_{1-3}$ and the solid-state switch device $S_{1-4}$ receive a third driving signal, the solid-state switch device $S_{1-1}$, the solid-state switch device $S_{1-2}$, the solid-state switch device $S_{1-3}$ and the solid-state switch device $S_{1-4}$ are all in a switch-off state. The diode $D_{1-1}$, the diode $D_{1-2}$, the diode $D_{1-3}$ and the diode $D_{1-4}$, and the diode $D_{2-1}$, the diode $D_{2-2}$, the diode $D_{2-3}$ and the diode $D_{2-4}$ all have an unidirectional conduction function, such that the capacitor $C_{1-1}$, the capacitor $C_{1-2}$, the capacitor $C_{1-3}$ and the capacitor $C_{1-4}$ have a parallel connection relationship and are all electrically connected to the first end and the second end of the first power supply U1, i.e., all being electrically connected to the positive electrode and the negative electrode of the first power supply U1. After charging is completed, the potential difference between two ends of each of the capacitor $C_{1-1}$, the capacitor $C_{1-2}$, the capacitor $C_{1-3}$ and the capacitor $C_{1-4}$ is the first voltage.

Similarly, referring to FIG. 6, when the solid-state switch device $S_{2-1}$, the solid-state switch device $S_{2-2}$, the solid-state switch device $S_{2-3}$ and the solid-state switch device $S_{2-4}$ all receive a fourth driving signal, the capacitor $C_{2-1}$, the capacitor $C_{2-2}$, the capacitor $C_{2-3}$ and the capacitor $C_{2-4}$ have a parallel connection relationship and are all electrically connected to the first end and the second end of the second power supply U2, i.e., all being electrically connected to the positive electrode and the negative electrode of the second power supply U2. After charging is completed, the potential difference between two ends of each of the capacitor $C_{2-1}$, the capacitor $C_{2-2}$, the capacitor $C_{2-3}$ and the capacitor $C_{2-4}$ is the second voltage.

As shown in FIG. 7, when the solid-state switch device $S_{1-1}$, the solid-state switch device $S_{1-2}$, the solid-state switch device $S_{1-3}$ and the solid-state switch device $S_{1-4}$ all receive the first driving signal, the solid-state switch device $S_{1-1}$, the solid-state switch device $S_{1-2}$, the solid-state switch device $S_{1-3}$ and the solid-state switch device $S_{1-4}$ are all in a switch-on state. Since the diode $D_{1-1}$, the diode $D_{1-2}$, the diode $D_{1-3}$ and the diode $D_{1-4}$, and the diode $D_{2-1}$, the diode $D_{2-2}$, the diode $D_{2-3}$ and the diode $D_{2-4}$ all have the unidirectional conduction function, the capacitor $C_{1-1}$, the capacitor $C_{1-2}$, the capacitor $C_{1-3}$ and the capacitor $C_{1-4}$ have a serial connection relationship, and the capacitor $C_{1-1}$, the capacitor $C_{1-2}$, the capacitor $C_{1-3}$ and the capacitor $C_{1-4}$ discharge electricity at the same time, with the discharge voltages all being the first voltage, such that the voltage of the formed first pulse signal is four times of the first voltage.

Similarly, as shown in FIG. 7, when the solid-state switch device $S_{2-1}$, the solid-state switch device $S_{2-2}$, the solid-state switch device $S_{2-3}$ and the solid-state switch device $S_{2-4}$ all receive the second driving signal, the solid-state switch device $S_{2-1}$, the solid-state switch device $S_{2-2}$, the solid-state switch device $S_{2-3}$ and the solid-state switch device $S_{2-4}$ are all in the switch-on state, the capacitor $C_{2-1}$, the capacitor $C_{2-2}$, the capacitor $C_{2-3}$ and the capacitor $C_{2-4}$ have the serial connection relationship, and the capacitor $C_{2-1}$, the capacitor $C_{2-2}$, the capacitor $C_{2-3}$ and the capacitor $C_{2-4}$ discharge electricity at the same time, with the discharge voltages all being the second voltage, such that the voltage of the formed second pulse signal is four times of the second voltage.

As shown in FIG. 8, in the pulse generation apparatus in the present embodiment, a driving circuit 2 includes an electro-optical conversion module 21, a signal processing module 23 and an optical fiber 22, which is connected to the electro-optical conversion module 21 and the signal processing module 23, respectively. The electro-optical conversion module 21 is electrically connected to a host computer 1, and the signal processing module 23 is electrically connected to the pulse generation circuit 3.

The electro-optical conversion module 21 is configured to receive a first control signal and a second control signal, convert the first control signal into a first optical driving signal, convert the second control signal into a second optical driving signal, and transmit the first optical driving signal and the second optical driving signal to the signal processing module 23 through the optical fiber 22.

The signal processing module 23 is configured to receive the first optical driving signal and the second optical driving signal, convert the first optical driving signal into a first electrical driving signal, convert the second optical driving signal into a second electrical driving signal, process the first electrical driving signal to obtain a first driving signal, process the second electrical driving signal to obtain a second driving signal, and transmit the first driving signal and the second driving signal to the pulse generation circuit 3.

The driving circuit 2 provided in the present embodiment converts a control signal into an optical driving signal, and then performs photoelectric conversion and processing on the optical driving signal so as to obtain a driving signal, such that a weak current part can be isolated from the strong-current pulse generation circuit 3, thereby reducing electromagnetic interference of the pulse generation circuit 3 on the weak current part, improving the accuracy of the driving signal, and thus improving the accuracy of the pulse signal.

In some embodiments, referring to FIG. 17, the electro-optical conversion module 21 includes a buffer unit 211, a first signal amplification unit 212 and a first conversion unit 213. The buffer unit is configured to receive a control signal and buffer the control signal.

Specifically, as shown in FIG. 18, the buffer unit 211 may be a multi-channel buffer which includes k signal buffer channels 2111, each of the signal buffer channels 211 being used for inputting of one control signal and storing the control signal, and k being an integer greater than 1. In a particular embodiment, the multi-channel buffer may be an eight-channel buffer of the model 74LVC245. Certainly, it is also possible to select other models of buffers that have different numbers of signal buffer channels according to specific implementation requirements.

It should be noted that the k signal buffer channels 2111 are not all receive the control signals at the same time, instead, it is possible that some of the signal buffer channels 2111 receive the control signals and further acquire driving signals by means of processing of a plurality of subsequent units.

As shown in FIG. 17, the first signal amplification unit 212 is electrically connected to the buffer unit 211, and is configured to perform amplification processing on the buffered control signal.

In some embodiments, referring to FIG. 18, the first signal amplification unit 212 may include k first amplification sub-units 2121. Each of the first amplification sub-units 2121 is electrically connected to one signal buffer channel 2111, and is used for performing amplification processing on the control signal stored in the corresponding signal buffer channel 2111. The "corresponding signal buffer channel 2111" mentioned in the present embodiment refers to the signal buffer channel 2111 that is electrically connected to the first amplification sub-unit 2121, and the "corresponding" in subsequent embodiments also refer to an electrical connection or communication connection being formed between the first amplification sub-unit and the signal buffer channel, which will not be described in the subsequent embodiments.

As shown in FIG. 17, the first conversion unit 213 is electrically connected to the first signal amplification unit 212 and the optical fiber 22, respectively, and is configured to perform electro-optical conversion on the amplified control signal to obtain an optical driving signal, and send same to the signal processing module 23 through the optical fiber 22.

In some embodiments, as shown in FIG. 18, the first conversion unit 213 is an optical signal transmitter which includes k electro-optical conversion channels 2311, each of the electro-optical conversion channels 2311 being electrically connected to one first amplification sub-unit 2121, and being used for converting the control signal amplified by the corresponding first amplification sub-unit 2121 into an optical driving signal, and transmitting the optical driving signal to the signal processing module 23 through the optical fiber 22. In a particular embodiment, the optical signal transmitter may be an optical fiber transmitter.

In the driving circuit 2 provided by the present embodiment, the described electro-optical conversion module 21 is used to buffer a control signal first, which is conducive to an increase in the transmission speed of the driving circuit 2, and then perform amplification processing on the control signal, such that the control signal is enhanced to reduce the influence of electromagnetic interference on the control signal.

As shown in FIG. 17, in the driving circuit 2 provided in the present embodiment, the signal processing module 23 includes a second conversion unit 231 and a second amplification unit 232.

The second conversion unit 231 is connected to the optical fiber 22, and is configured to receive the optical driving signal and convert the optical driving signal into an electrical driving signal. Specifically, as shown in FIG. 18, the second conversion unit 231 is an optical signal receiver which includes k photoelectric conversion channels 2311, each of the photoelectric conversion channels 2311 being used for receiving one optical driving signal and converting the optical driving signal into the electrical driving signal. In a particular embodiment, the optical signal receiver is an optical fiber receiver. Moreover, based on the specific structure of the electro-optical conversion module 21 in the above embodiment, each of the photoelectric conversion channel 2311 is in communication connection with one electro-optical conversion channel 2311 through the optical fiber.

As shown in FIG. 17, the second signal amplification unit 232 is electrically connected to the second conversion unit 231, and is configured to perform amplification processing on the electrical driving signal to obtain a driving signal. Specifically, as shown in FIG. 18, the second signal amplification unit 232 includes k second amplification sub-units 2321, each of the second amplification sub-units 2321 being electrically connected to one second conversion unit 231 by means of the photoelectric conversion channel 2311, and being used for performing amplification processing on the corresponding electrical driving signal to obtain the driving signal.

In the driving circuit 2 provided by the present embodiment, the described signal processing module 23 is used to perform amplification processing on the electrical driving signal, such that the control signal is further enhanced to reduce the influence of electromagnetic interference on the control signal.

As shown in FIG. 17, in the driving circuit 2 provided in the present embodiment, the signal processing module 23 may further include a first filter unit 233 and a second filter unit 234.

As shown in FIG. 17, the first filter unit 233 is electrically connected to the second conversion unit 231 and the second signal amplification unit 232, respectively, and is configured to perform first filter processing on the electrical driving signal. Specifically, as shown in FIG. 18, the first filter unit 233 includes k first filter sub-units 2331, each of the first filter sub-units 2331 being electrically connected to one photoelectric conversion channel 2311, and being used for performing first filter processing on the electrical driving signal converted by the corresponding photoelectric conversion channel 2311. In a particular embodiment, the first filter unit 233 is an RC filter circuit.

As shown in FIG. 17, a second filter unit 234 is electrically connected to the second signal amplification unit 232 and the pulse generation circuit 3, respectively, and is configured to perform second filtering processing on the driving signal and send the driving signal subjected to second filtering processing to the pulse generation circuit 3. Specifically, as shown in FIG. 18, the second filter unit 234 includes k second filter sub-units 2341, each of the second filter sub-unit 2341 being electrically connected to one second amplification sub-unit 2321, and being used for performing second filtering processing on the electrical driving signal obtained by means of amplification processing by the corresponding second amplification sub-unit 2321, and sending the driving signal subjected to second filtering processing to the pulse generation circuit 3. In a particular embodiment, the second filter unit 234 is an RC filter circuit.

Before the described two filter units are added, the pulse formed by the pulse generation circuit 3 has relatively large stretching, whereas after the described two filter units are added, high-frequency interference can be removed, and the pulse formed by the pulse generation circuit 3 has no stretching. Hence, through the addition of the described two filter units, the driving circuit 2 provided by the present embodiment can further reduce the influence of electromagnetic interference on the driving signal.

As shown in FIG. 9, the pulse generation apparatus in the present embodiment further includes a circuit board PCB which includes a first part 10 and a second part 20, which is located at a side of the first part 10. The driving circuit 2 is arranged at the first part 10, and the pulse generation circuit 3 is arranged at the second part 20.

Alternatively, as shown in FIG. 10, the circuit board includes a first circuit board PCB1 and a second circuit board PCB1. The driving circuit 2 is arranged at the first circuit board PCB1, and the pulse generation circuit 3 is arranged at the second circuit board PCB2.

The pulse generation circuit 3 can be separated from the driving circuit 2 as far as possible by means of fabricating the driving circuit 2 and the pulse generation circuit 3 at different parts of the circuit board PCB or fabricating same on different circuit boards. Such design is conducted since the intersection of the wiring of the driving circuit 2 and the wiring of the pulse generation circuit 3 may result in intense electromagnetic coupling and an increase in parasitic parameters between electronic components such that relatively large interference may occur in the driving circuit 2, causing a signal distortion in the driving circuit 2, and thus the waveform quality of a pulse generated by a main circuit deteriorates. The separation of the pulse generation circuit 3 from the driving circuit 2 may significantly reduce interference of the pulse generation circuit 3 on the driving circuit 2.

As shown in FIG. 11, the pulse generation apparatus in the present embodiment further includes a shielding structure M which is connected to the circuit board PCB. The driving circuit 2 is located in the shielding structure M. Specifically, the shielding structure M is a metal shielding cover. The metal shielding cover is fixed to the circuit board PCB so that the electro-optical conversion module 21 is located in the metal shielding cover, or the metal shielding cover is fixed to the first circuit board PCB so that the electro-optical conversion module 21 is located in the metal shielding cover.

As shown in FIG. 12 and FIG. 13, before the shielding structure M is not provided in an existing technique, waveform collapse occurs in a pulse signal generated by a pulse generation circuit 3, whereas in the pulse generation apparatus provided in the present embodiment, after the shielding structure M is provided, the waveform collapse of the pulse signal formed by the pulse generation circuit 3 is significantly alleviated.

Based on the same inventive concept, an embodiment of the present application further provides a synergistic pulse generation device which includes a host computer 1 and the synergistic pulse generation apparatus in the above embodiment as shown in FIG. 1. The host computer 1 is configured to generate a first control signal and a second control signal according to an inputted instruction.

The synergistic pulse generation device provided in the present embodiment has the beneficial effects of the synergistic pulse generation circuit 3 in the embodiments above, which will not be described in details here.

Specifically, the host computer 1 may be a computer, and the inputted instruction may be parameters of the first control signal and the second control signal, for example, may be voltages, periods, durations of the effective level, etc. of the first control signal and the second control signal. The inputted instruction may also be parameters of the first driving signal and the second driving signal, for example, may be voltages, periods, pulse widths, etc. of the first driving signal and the second driving signal.

When the synergistic pulse generation device provided in the present embodiment is an electroablation device capable of synergistically outputting a microsecond pulse/millisecond pulse signal and a nanosecond pulse, the first pulse signal is the millisecond pulse/microsecond pulse signal, and the second pulse signal is the nanosecond pulse signal. Then, the inputted instruction may be the width, number, voltage, etc. of required pulses, and may also be parameters of a tumor tissue. The correlation between the parameters of the tumor tissue and the parameters of the required pulses is stored in the electroablation device, and a combination of nanosecond pulses and microsecond pulses/millisecond pulses generated according to the parameters of the tumor tissue is applied to the tumor tissue, such that the ablation effect on the tumor tissue can be effectively improved.

Based on the same inventive concept, an embodiment of the present application further provides a synergistic pulse generation method. As shown in FIG. 1 and FIG. 14, the synergistic pulse generation method includes:

S1: a first pulse generation module 31 storing electric energy supplied by a first power supply, and a second pulse generation module 32 storing electric energy supplied by a second power supply. It should be noted that a charging process of the first pulse generation module 31 and a charging process of the second pulse generation module 32 may be conducted at the same time, and it is also possible to only charge the first pulse generation module 31 or the second pulse generation module 32, or that the charging process of the first pulse generation module 31 and the charging process of the second pulse generation module 32 are not conducted at the same time.

The method further includes: S2: a driving circuit 2 receiving a first control signal sent by a host computer 1 and converting the first control signal into a first driving signal, and the driving circuit 2 receiving a second control signal sent by the host computer 1 and converting the second control signal into a second driving signal; and S3: the first pulse generation module 31 receiving the first driving signal and discharging electricity under the control of the first driving signal to form a first pulse signal applied to a load 4, and a second pulse generation module 32 receiving the second driving signal and discharging electricity under the control of the second driving signal to form a second pulse signal applied to the load 4.

In some embodiments, the voltage of the second power supply is greater than the voltage of the first power supply, the width of the second pulse signal is smaller than the width of the first pulse signal, and the time when the second pulse generation module 32 receives the second driving signal is different from the time when the first pulse generation module 31 receives the first driving signal.

By means of the synergistic pulse generation method provided in the embodiments of the present application, a driving circuit 2 respectively converts a first control signal and a second control signal, which are sent by a host computer 1, into a first driving signal and a second driving signal, and a pulse generation circuit 3 can selectively form a first pulse signal and/or a second pulse signal of different widths according to the first driving signal and the second driving signal, so as to achieve the purpose of applying a composite pulse signal to a load 4. Taking the load 4 being tumor cells as an example, the action of a composite pulse is conducive to an improvement in the ablation effect on the tumor cells.

Optionally, as shown in FIG. 2, n stages of first pulse generation units 311 included in the first pulse generation module 31 receive electric energy supplied by the first power supply U1 and store same, and m stages of second pulse generation units 321 included in the second pulse generation module 32 receive electric energy supplied by the second power supply U2 and store same. n is an integer greater than or equal to 1, and m is an integer greater than or equal to 1. Based on this, step S1 includes: first switch units 3112 being switched off when receiving a third driving signal, so that stages of first storage units 3111 are connected to the first power supply U1 in parallel to receive electric energy supplied by the first power supply U1 and store same; and second switch units 3212 being switched off when receiving a fourth driving signal, so that stages of second storage units 3211 are connected to the second power supply U2 in parallel to receive electric energy supplied by the second power supply U2 and store same.

Taking the synergistic pulse generation circuit 3 shown in FIG. 6 as an example, the charging process of the first pulse generation module 31 is as follows: when a solid-state switch device $S_{1-1}$, a solid-state switch device $S_{1-2}$, a solid-state switch device $S_{1-3}$ and a solid-state switch device $S_{1-4}$ receive the third driving signal, the solid-state switch device $S_{1-1}$, the solid-state switch device $S_{1-2}$, the solid-state switch device $S_{1-3}$ and the solid-state switch device $S_{1-4}$ are all in a switch-off state; a diode $D_{1-1}$, a diode $D_{1-2}$, a diode $D_{1-3}$ and a diode $D_{1-4}$, and a diode $D_{2-1}$, a diode $D_{2-2}$, a diode $D_{2-3}$ and a diode $D_{2-4}$ all have an unidirectional conduction function, such that a capacitor $C_{1-1}$, a capacitor $C_{1-2}$, a capacitor $C_{1-3}$ and a capacitor $C_{1-4}$ have a parallel connection relationship and are all electrically connected to a first end and a second end of the first power supply U1, i.e., all being electrically connected to the positive electrode and the negative electrode of the first power supply U1; and the charging of the first pulse generation module 31 is completed until the potential difference between two ends of each of the capacitor $C_{1-1}$, the capacitor $C_{1-2}$, the capacitor $C_{1-3}$ and the capacitor $C_{1-4}$ is the first voltage.

Taking the synergistic pulse generation circuit 3 shown in FIG. 6 as an example, the charging process of the second pulse generation module 32 is as follows: when a solid-state switch device $S_{2-1}$, a solid-state switch device $S_{2-2}$, a solid-state switch device $S_{2-3}$ and a solid-state switch device $S_{2-4}$ receive a fourth driving signal, the solid-state switch device $S_{2-1}$, the solid-state switch device $S_{2-2}$, the solid-state switch device $S_{2-3}$ and the solid-state switch device $S_{24}$ are all in a switch-off state; a diode $D_{3-1}$, a diode $D_{3-2}$, a diode $D_{3-3}$ and a diode $D_{3-4}$, and a diode $D_{4-1}$, a diode $D_{4-2}$, a diode $D_{4-3}$ and a diode $D_{4-4}$ all have an unidirectional conduction function, such that a capacitor $C_{2-1}$, a capacitor $C_{2-2}$, a capacitor $C_{2-3}$ and a capacitor $C_{2-4}$ have a parallel connection relationship and are all electrically connected to a first end and a second end of the second power supply U2, i.e., all being electrically connected to the positive electrode and the negative electrode of the second power supply U2; and the charging of the second pulse generation module 32 is completed until the potential difference between two ends of each of the capacitor $C_{2-1}$, the capacitor $C_{2-2}$, the capacitor $C_{2-3}$ and the capacitor $C_{2-4}$ is the second voltage.

In a particular embodiment, the first driving signal and the second driving signal are both at a high level, and the third driving signal and the fourth driving signal are both at a low level. That is, as long as the first pulse generation module 31 does not receive the first driving signal, the first power supply U1 is in the state of charging the stages of the first capacitors or the state of maintaining the voltage difference between two ends of each stage of the first capacitor to be the first voltage. Similarly, as long as the second pulse generation module 32 does not receive the second driving signal, the second power supply U2 is in the state of charging the stages of the second capacitors or the state of maintaining the voltage difference between two ends of each stage of the second capacitor to be the second voltage. Certainly, it should be understood by those skilled in the art that the level of each driving signal can also be adaptively set correspondingly according to different selection of solid-state switch devices.

Optionally, as shown in FIG. 8 and FIG. 15, in the synergistic pulse generation method provided in the present embodiment, step S2 includes:

S201, an electro-optical conversion module 21 receiving a first control signal and a second control signal, converting the first control signal into a first optical driving signal, converting the second control signal into a second optical driving signal, and transmitting the first optical driving signal and the second optical driving signal to a signal processing module 23 through an optical fiber 22; and S202, the signal processing module 23 receiving the first optical driving signal and the second optical driving signal, converting the first optical driving signal into a first electrical driving signal, converting the second optical driving signal into a second electrical driving signal, processing the first electrical driving signal to obtain a first driving signal, processing the second electrical driving signal to obtain a second driving signal, transmitting the first driving signal to the first pulse generation module 31, and transmitting the second driving signal to the second pulse generation module 32.

By means of the synergistic pulse generation method provided in the present embodiment, a control signal is converted into an optical driving signal, and photoelectric conversion and processing are then performed on the optical driving signal so as to obtain a driving signal, such that a weak current circuit can be isolated from the strong-current pulse generation circuit 3, thereby reducing electromagnetic interference of the pulse generation circuit 3 on the weak current circuit, improving the accuracy of the driving signal, and thus improving the accuracy of the pulse signal.

Optionally, as shown in FIG. 2 and FIG. 16, the synergistic pulse generation method provided in the present embodiment, step S3 includes:

S301, x first pulse generation pulse units 311 receiving the first driving signal, and discharging electricity under the control of the first driving signal to form the first pulse signal.

As shown in FIG. 7, when the solid-state switch device $S_{1-1}$, the solid-state switch device $S_{1-2}$, the solid-state switch device $S_{1-3}$ and the solid-state switch device $S_{1-4}$ all receive the first driving signal, the solid-state switch device $S_{1-1}$, the solid-state switch device $S_{1-2}$, the solid-state switch device $S_{1-3}$ and the solid-state switch device $S_{1-4}$ are all in a switch-on state. Since the diode $D_{1-1}$, the diode $D_{1-2}$, the diode $D_{1-3}$ and the diode $D_{1-4}$, and the diode $D_{2-1}$, the diode $D_{2-2}$, the diode $D_{2-3}$ and the diode $D_{2-4}$ all have the unidirectional conduction function, the capacitor $C_{1-1}$, the capacitor $C_{1-2}$, the capacitor $C_{1-3}$ and the capacitor $C_{1-4}$ have a serial connection relationship, and the capacitor $C_{1-1}$, the capacitor $C_{1-2}$, the capacitor $C_{1-3}$ and the capacitor $C_{1-4}$ discharge electricity at the same time, with the discharge voltages all being the first voltage, such that the voltage of the formed pulse is four times of the first voltage.

The method further includes $S_{320}$: y second pulse generation units 321 receiving the second driving signal, and discharging electricity under the control of the second driving signal to form the second pulse signal.

As shown in FIG. 7, when the solid-state switch device $S_{2-1}$, the solid-state switch device $S_{2-2}$, the solid-state switch device $S_{2-3}$ and the solid-state switch device $S_{24}$ all receive the second driving signal, the solid-state switch device $S_{2-1}$, the solid-state switch device $S_{2-2}$, the solid-state switch device $S_{2-3}$ and the solid-state switch device $S_{2-4}$ are all in the switch-on state, the capacitor $C_{2-1}$, the capacitor $C_{2-2}$, the capacitor $C_{2-3}$ and the capacitor $C_{2-4}$ have the serial connection relationship, and the capacitor $C_{2-1}$, the capacitor $C_{2-2}$, the capacitor $C_{2-3}$ and the capacitor $C_{2-4}$ discharge electricity at the same time, with the discharge voltages all being the second voltage, such that the voltage of the formed second pulse is four times of the second voltage.

The method further includes S303: applying the first pulse signal and/or the second pulse signal to the load 4.

In an optional embodiment, as shown in FIG. 4, based on the synergistic pulse generation apparatus including an output module 7, step S303 specifically includes: applying the first pulse and/or the second pulse to the load 4 under the control of a trigger instruction. Specifically, for the output module 7, reference can be made to the above embodiments of the synergistic pulse generation apparatus, which will not be described in details here.

In some optional embodiment, as shown in FIG. 4, based on the synergistic pulse generation apparatus including a resistor 8 and a monitoring module 9, the synergistic pulse generation method provided in the present embodiment further includes: applying the first pulse signal and/or the second pulse signal to the resistor 8, and also monitoring the current and voltage applied to the resistor 8 by the first pulse signal and/or the second pulse signal. Specifically, for the resistor 8 and the monitoring module 9, reference can be made to the above embodiments of the synergistic pulse generation apparatus, which will not be described in details here.

In some optional embodiments, as shown in FIG. 4, based on the synergistic pulse generation apparatus including a first discharge module 5 and a second discharge module 6, the synergistic pulse generation method provided in the present embodiment further includes: receiving a first discharge signal and connecting the first pulse generation module 31 to the ground under the control of the first discharge signal to release residual electricity in the first pulse generation module 31; and receiving a second discharge signal and connecting the second pulse generation module 32 to the ground under the control of the second discharge signal to release residual electricity in the second pulse generation module 32. Specifically, for the first discharge module 5 and the second discharge module 6, reference can be made to the above embodiments of the synergistic pulse generation apparatus, which will not be described in details here.

By means of the embodiments of the present application, at least the following beneficial effects can be achieved: by means of the synergistic pulse generation apparatus, device and method provided in the embodiments of the present application, a driving circuit respectively converts a first control signal and a second control signal, which are sent by a host computer, into a first driving signal and a second driving signal, and a pulse generation circuit can selectively form a first pulse signal and/or a second pulse signal of different widths according to the first driving signal and the second driving signal, so as to achieve the purpose of applying a composite pulse signal to a load. Taking the load being tumor cells as an example, the action of a composite pulse is conducive to an improvement in the ablation effect on the tumor cells.

The terms "first" and "second" are used for descriptive purposes only, and cannot be construed as indicating or implying relative importance or implicitly indicating the number of technical features indicated. Thus, the features defined with "first" and "second" may explicitly or implicitly include one or more features. In the description of the present application, unless otherwise specified, "a plurality of" means two or more.

In the description of the present application, it should be noted that, unless otherwise explicitly specified and defined, the terms "mounting", "connecting" and "connection" should be understood in a broad sense, for example, they may be a fixed connection, a detachable connection, or an integrated connection; and can be directly connected, or indirectly connected by means of an intermediate medium, or communication between interiors of two elements. For those of ordinary skill in the art, the specific meaning of the terms mentioned above in the present application can be construed according to specific circumstances.

In the description of the present specification, the specific features, structures, materials or characteristics may be combined in a suitable manner in any one or more embodiments or examples.

The above merely describes some embodiments of the present application, and it should be noted that for persons of ordinary skill in the art, several improvements and modifications can also be made without departing from the principle of the present application, and these improvements and modifications are also considered to be within the scope of protection of the present application.

What is claimed is:

1. A synergistic pulse generation apparatus for generating a pulse signal under the control of a host computer, comprising:

a driving circuit, which is electrically connected to the host computer, and is configured to receive a first control signal sent by the host computer and convert the first control signal into a first driving signal, and receive a second control signal sent by the host computer and convert the second control signal into a second driving signal; and a pulse generation circuit, which comprises a first power supply, a first pulse generation module, which is electrically connected to the first power supply, a second power supply, and a second pulse generation module, which is electrically connected to the second power supply, wherein the first pulse generation module is configured to store electric energy supplied by the first power supply, and discharge electricity under the control of the first driving signal to form a first pulse signal applied to a load; and the second pulse generation module is configured to store electric energy supplied by the second power supply, and discharge electricity under the control of the second driving signal to form a second pulse signal applied to the load, wherein the voltage of the second power supply is greater than the voltage of the first power supply, and the width of the second pulse signal is less than the width of the first pulse signal, wherein the driving circuit comprises an electro-optical conversion module, a signal processing module and an optical fiber, which is electrically connected to the electro-optical conversion module and the signal processing module, respectively, wherein the electro-optical conversion module is electrically connected to the host computer, and the signal processing module is electrically connected to the pulse generation circuit;

the electro-optical conversion module is configured to receive the first and second control signals sent by the host computer, convert the first and second control signals into first and second optical driving signals and send same to the signal processing module by means of the optical fiber; and the signal processing module is configured to receive the first and second optical driving signals and convert the first and second optical driving signals into first and second electrical driving signals, process the first and second electrical driving signals to obtain the first and second driving signals, and transmit the first and second driving signals to the pulse generation circuit, wherein the electro-optical conversion module comprises:

a buffer unit, which is electrically connected to the host computer, and is configured to receive the first and second control signals and buffer the first and second control signals;

a first signal amplification unit, which is electrically connected to the buffer unit, and is configured to perform amplification processing on the buffered first and second control signals; and a first conversion unit, which is electrically connected to the first signal amplification unit and the optical fiber, respectively, and is configured to perform electro-optical conversion on the first and second control signals that have been subjected to amplification processing, so as to obtain the first and second optical driving signals, and send same to the signal processing module by means of the optical fiber, and wherein the signal processing module comprises:

a second conversion unit, which is connected to the optical fiber and is configured to receive the first and second optical driving signals and convert the first and second optical driving signals into the first and second electrical driving signals;

a first filter unit, which is electrically connected to the second conversion unit and is configured to perform first filtering processing on the first and second electrical driving signals;

a second signal amplification unit which is electrically connected to the first filter unit, and is configured to perform amplification processing on the filtered first and second electrical driving signals to obtain third and fourth driving signals; and a second filter unit, which is electrically connected to the second signal amplification unit and the pulse generation circuit, respectively, and is configured to perform second filtering processing on the third and fourth driving signals and send the third driving signal subjected to second filtering processing as the first driving signal and the fourth driving signal subjected to second filtering processing as the second driving signal to the pulse generation circuit, wherein the driving circuit is configured to perform operations of buffering, amplifying and converting the first and second control signals into the first and second optical driving signals by the electro-optical conversion module and to perform operations of converting the first and second optical driving signals into the first and second electrical driving signals, and amplifying and filtering the first and second electrical driving signals to obtain the first and second driving signals by the signal processing module, so as to reduce influence of electromagnetic interference from the pulse generation circuit on the first and second driving signals.

2. The synergistic pulse generation apparatus according to claim 1, wherein the pulse generation circuit further comprises:

a first discharge module, which is electrically connected to the first pulse generation module and a ground, respectively, and is configured to connect the first pulse generation module to the ground under the control of a first discharge signal to release residual electricity in the first pulse generation module; and a second discharge module, which is electrically connected to the second pulse generation module and the ground, respectively, and is configured to connect the second pulse generation module to the ground under the control of a second discharge signal to release residual electricity in the second pulse generation module.

3. The synergistic pulse generation apparatus according to claim 1, wherein the pulse generation circuit further comprises:

an output module, which comprises a trigger unit and at least a pair of electrodes, which are electrically connected to the trigger unit, wherein the trigger unit is electrically connected to the first pulse generation module and the second pulse generation module, respectively, the electrodes are in contact with the load, and when triggered by a trigger instruction, the trigger unit is configured to be switched on so that the first pulse signal and/or the second pulse signal are/is transmitted to the electrodes.

4. The synergistic pulse generation apparatus according to claim 1, wherein the pulse generation circuit further comprises:

a resistor, which is electrically connected to the first pulse generation module, the second pulse generation module and the ground, respectively, wherein the first pulse signal and/or the second pulse signal are/is also applied to the resistor; and a monitoring module, which comprises a first monitoring unit and a second monitoring unit, wherein the first monitoring unit is configured to monitor currents outputted by the first pulse signal and the second pulse signal; and the second monitoring unit is configured to monitor voltages applied to the resistor by the first pulse signal and the second pulse signal.

5. The synergistic pulse generation apparatus according to claim 1, further comprising a circuit board, wherein the circuit board comprises a first part and a second part, which is located at a side of the first part, the driving circuit is arranged at the first part, and the pulse generation circuit is arranged at the second part; or the circuit board comprises a first circuit board and a second circuit board, the driving circuit is arranged at the first circuit board, and the pulse generation circuit is arranged at the second circuit board.

6. The synergistic pulse generation apparatus according to claim 5, further comprising: a shielding structure, which is arranged on the circuit board, wherein the driving circuit is located inside the shielding structure.

7. The synergistic pulse generation apparatus according to claim 1, wherein the first pulse signal is a microsecond pulse signal or a millisecond pulse signal, and the second pulse signal is a nanosecond pulse signal.

8. The synergistic pulse generation apparatus according to claim 1, wherein the buffer unit is a multi-channel buffer which comprises k signal buffer channels, each of the signal buffer channels being used for inputting of one of the first and second control signals and storing the one of the first and second control signals, and k being an integer greater than 1;

the first signal amplification unit comprises k first amplification sub-units, each of the first amplification sub-units being electrically connected to one signal buffer channel, and the first amplification sub-unit being used for performing amplification processing on the one of the first and second control signals stored in the corresponding signal buffer channel; and the first conversion unit is an optical signal transmitter which comprises k electro-optical conversion channels, each of the electro-optical conversion channels being electrically connected to one first amplification sub-unit, and the electro-optical conversion channel being used for converting, into the first or second optical driving signal, the one of the first and second control signals subjected to amplification processing of the corresponding first amplification sub-unit, and transmitting the first or second optical driving signal to the signal processing module by means of the optical fiber.

9. The synergistic pulse generation apparatus according to claim 1, wherein the second conversion unit is an optical signal receiver which comprises k photoelectric conversion channels, each of the photoelectric conversion channels being used for receiving one of the first and second optical driving signals and converting the one of the first and second optical driving signals into the first or second electrical driving signal, and k being an integer greater than 1;

the first filter unit comprises k first filter sub-units, each of the first filter sub-units being electrically connected to one photoelectric conversion channel, and the first filter sub-unit being used for performing first filtering processing on the first or second electrical driving signal obtained by means of conversion by the corresponding photoelectric conversion channel;

the second signal amplification unit comprises k second amplification sub-units, each of the second amplification sub-units being electrically connected to one first filter sub-unit, and the second amplification sub-unit being used for performing amplification processing on the first or second electrical driving signal subjected to first filtering processing of the corresponding first filter sub-unit, so as to obtain the third or fourth driving signal; and the second filter unit comprises k second filter sub-units, each of the second filter sub-units being electrically connected to one second amplification sub-unit, and the second filter sub-unit being used for performing second filtering processing on the third or fourth driving signal obtained by means of amplification processing by the corresponding second amplification sub-unit, and sending the third driving signal subjected to second filtering as the first driving signal or the fourth driving signal subjected to second filtering as the second driving signal to the pulse generation circuit.

10. The synergistic pulse generation apparatus according to claim 1, wherein the first pulse generation module comprises n stages of first pulse generation units configured to receive electric energy supplied by the first power supply with a first voltage and store same, and release stored electric energy when receiving a first control signal, so that x first pulse generation units receiving the first control signal discharge electricity to form a first pulse signal applied to a load, wherein n is an integer greater than or equal to 1, and x is an integer greater than or equal to 1 and less than or equal to n;

the second pulse generation module comprises m stages of second pulse generation units configured to receive electric energy supplied by the second power supply with a second voltage and store same, and release stored electric energy when receiving a second control signal, so that y second pulse generation units receiving the second control signal discharge electricity to form a second pulse signal applied to the load, wherein m is an integer greater than or equal to 1, and y is an integer greater than or equal to 1 and less than or equal to m; and the second voltage is greater than the first voltage.

11. The synergistic pulse generation apparatus according to claim 10, wherein the first pulse generation units each comprise a first storage unit, a first switch unit and a first cutoff unit, wherein the first switch units are configured to receive the first control signal and switch on under the control of the first control signal, so that the respective first storage units at the same stages as those of the first switch units receiving the first control signal are connected in series and discharge electricity so as to form the first pulse signal, and each of the first cutoff units is configured to only allow a charging current to flow from the first power supply to the respective first pulse generation unit, or flow from the current stage of the first pulse generation unit to the next stage of a first pulse generation unit, and only allow a discharging current to flow from the current stage of the first pulse generation unit to the next stage of the first pulse generation unit; and the second pulse generation units each comprise a second storage unit, a second switch unit and a second cutoff unit, wherein the second switch units are configured to receive the second control signal and switch on under the control of the second control signal, so that the respective second storage units at the same stages as those of the second switch units receiving the second control signal are connected in series and discharge electricity so as to form the second pulse, and the second cutoff unit is configured to only allow a charging current to flow from the second power supply to the second pulse generation unit, or flow from the current stage of the second pulse generation unit to the next stage of the second pulse generation unit, and only allow a discharging current to flow from the current stage of the second pulse generation unit to the next stage of the second pulse generation unit.

12. The synergistic pulse generation apparatus according to claim 11, wherein the first cutoff unit comprises a first cutoff device and a second cutoff device, a first-stage first cutoff device is electrically connected to a first end of the first power supply and a first end of a first-stage first storage unit, respectively, an ith-stage first cutoff device is electrically connected to a first end of an (i−1)th-stage first storage unit, a first end of an ith-stage first storage unit and an (i−1)th-stage first cutoff device, respectively, each stage of a second cutoff device is electrically connected to a second end of the current stage of a first storage unit, a second end of the current stage of a first switch unit and the next stage of a second cutoff device, respectively, and i is an integer greater than or equal to 2; and the second cutoff units comprise a third cutoff device and a fourth cutoff device, a first-stage third cutoff device is electrically connected to a first end of the second power supply and a first end of a first-stage second storage unit, respectively, a jth-stage third cutoff device is electrically connected to a first end of a (j−1)th-stage second storage unit, a first end of a jth-stage second storage unit and a (j−1)th-stage third cutoff device, respectively, each stage of a fourth cutoff device is electrically connected to a second end of the current stage of a second storage unit, a second end of the current stage of a second switch unit and the next stage of a fourth cutoff device, respectively, and j is an integer greater than or equal to 2.

13. The synergistic pulse generation apparatus according to claim 12, wherein the first storage unit comprises a first capacitor, and the second storage unit comprises a second capacitor;

the first switch unit comprises a first solid-state switch device, and the second switch unit comprises a second solid-state switch; and the first cutoff device comprises a first diode, the second cutoff device comprises a second diode, the third cutoff device comprises a third diode, and the fourth cutoff device comprises a fourth diode.

14. The synergistic pulse generation apparatus according to claim 11, wherein two ends of each stage of the first storage unit are electrically connected to two ends of the first power supply, respectively, a control end of each stage of the first switch unit is configured to receive the first control signal, and the first end and the second end of each stage of the first switch unit are electrically connected to the first end of the current stage of the first storage unit and the second end of the next stage of the first storage unit, respectively; and two ends of each stage of the second storage unit are electrically connected to two ends of the second power supply, respectively, a control end of each stage of the second switch unit is configured to receive the second control signal, and the first end and the second end of each stage of the second switch unit are electrically connected to the first end of the current stage of the second storage unit and the second end of the next stage of the second storage unit, respectively.

15. A synergistic pulse generation device, comprising:

a host computer configured to generate a first control signal and a second control signal according to an inputted instruction; and a synergistic pulse generation apparatus according to claim 1.

16. The synergistic pulse generation device according to claim 15, wherein the synergistic pulse generation device is an electroablation device; and a first pulse signal generated by the synergistic pulse generation apparatus is a microsecond pulse signal or a millisecond pulse signal, and a second pulse signal generated by the synergistic pulse generation apparatus is a nanosecond pulse signal.

17. A synergistic pulse generation method used for the synergistic pulse generation apparatus according to claim 1, the method comprising:

a first pulse generation module storing electric energy supplied by a first power supply, and a second pulse generation module storing electric energy supplied by a second power supply;

a driving circuit receiving a first control signal sent by a host computer and converting the first control signal into a first driving signal, and the driving circuit receiving a second control signal sent by the host computer and converting the second control signal into a second driving signal; and a first pulse generation module receiving the first driving signal and discharging electricity under the control of the first driving signal to form a first pulse signal applied to a load, and a second pulse generation module receiving the second driving signal and discharging electricity under the control of the second driving signal to form a second pulse signal applied to the load, wherein the voltage of the second power supply is greater than the voltage of the first power supply, and the width of the second pulse signal is less than the width of the first pulse signal, wherein the driving circuit receiving a first control signal sent by a host computer and converting the first control signal into a first driving signal, comprises operations of:

S1: a buffer unit receiving and buffering the first control signal;

S2: a first signal amplification unit performing amplification processing on the buffered first control signal;

S3: a first conversion unit performing electro-optical conversion on the first control signal that has been subjected to amplification processing, so as to obtain a first optical driving signal, and send same to a second conversion unit by means of an optical fiber;

S4: the second conversion unit receiving the first optical driving signal and converting the first optical driving signal into a first electrical driving signal;

S5: a first filter unit performing first filtering processing on the first electrical driving signal;

S6: a second signal amplification unit performing amplification processing on the first electrical driving signal to obtain a third driving signal; and S7: a second filter unit performing second filtering processing on the third driving signal and send the third driving signal subjected to second filtering processing as the first driving signal to the pulse generation circuit, and wherein the driving circuit receiving a second control signal sent by the host computer and converting the second control signal into a second driving signal, comprises operations of:

S1': the buffer unit receiving and buffering the second control signal;

S2': the first signal amplification unit performing amplification processing on the buffered second control signal;

S3': the first conversion unit performing electro-optical conversion on the second control signal that has been subjected to amplification processing, so as to obtain a second optical driving signal, and send same to the second conversion unit by means of the optical fiber;

S4': the second conversion unit receiving the second optical driving signal and converting the second optical driving signal into a second electrical driving signal;

S5': the first filter unit performing first filtering processing on the second electrical driving signal;

S6': the second signal amplification unit performing amplification processing on the second electrical driving signal to obtain a fourth driving signal; and S7': the second filter unit performing second filtering processing on the fourth driving signal and send the fourth driving signal subjected to second filtering processing as the second driving signal to the pulse generation circuit, wherein in the method, the operations of S1-S7 and S1'-S7' allow to reduce influence of electromagnetic interference from the first pulse generation module and the second pulse generation module on the first driving signal and the second driving signal.

* * * * *